US011348011B2

(12) United States Patent
Bernert et al.

(10) Patent No.: US 11,348,011 B2
(45) Date of Patent: May 31, 2022

(54) METHOD FOR UNSUPERVISED SORTING IN REAL TIME OF ACTION POTENTIALS OF A PLURALITY OF BIOLOGICAL NEURONS

(71) Applicants: COMMISSARIAT À L'ÉNERGIE ATOMIQUE ET AUX ÉNERGIES ALTERNATIVES, Paris (FR); INSTITUT NATIONAL DE LA SANTE ET DE LA RECHERCHE MEDICALE, Paris (FR)

(72) Inventors: Marie Bernert, Grenoble (FR); Elisa Vianello, Grenoble (FR); Blaise Yvert, Saint Egreve (FR)

(73) Assignees: COMMISSARIAT A L'ENERGIE ATOMIQUE ET AUX ENERGIES ALTERNATIVES, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 1323 days.

(21) Appl. No.: 15/598,793

(22) Filed: May 18, 2017

(65) Prior Publication Data
US 2017/0337473 A1 Nov. 23, 2017

(30) Foreign Application Priority Data

May 19, 2016 (FR) ...................................... 1654485

(51) Int. Cl.
*G06N 3/08* (2006.01)
*A61B 5/00* (2006.01)
(Continued)

(52) U.S. Cl.
CPC ............... *G06N 3/088* (2013.01); *A61B 5/24* (2021.01); *A61B 5/7264* (2013.01); *G06N 3/049* (2013.01)

(58) Field of Classification Search
CPC ............................. G06N 3/088; G06N 3/049
(Continued)

(56) References Cited

U.S. PATENT DOCUMENTS

2009/0216091 A1 8/2009 Arndt

FOREIGN PATENT DOCUMENTS

WO    WO 2014/025765 A2    2/2014

OTHER PUBLICATIONS

Zhang et al. ("A Neuromorphic Neural Spike Clustering Processor for Deep-Brain Sensing and Stimulation Systems" 2015) (Year: 2015).*

(Continued)

*Primary Examiner* — Lut Wong
(74) *Attorney, Agent, or Firm* — Pillsbury Winthrop Shaw Pittman LLP

(57) ABSTRACT

A method for unsupervised sorting, in real time, of action potentials of biological neurons by a network of artificial neurons including input, intermediate and output layers, the method according to which: the input layer receives an electrical signal measuring an electrical activity of biological neurons, the electrical signal having a variable amplitude as a function of action potentials emitted by the plurality of biological neurons over time; the input layer converts the amplitude of the electrical signal into a train of first spikes; the input layer transmits the train of first spikes to the intermediate layer; the intermediate layer converts the train of first spikes into a train of second spikes; the intermediate layer transmits the train of second spikes to the output layer; as a function of the train of second spikes, the output layer (Continued)

sorts each occurrence of each type of action potential present in the electrical signal.

15 Claims, 8 Drawing Sheets

(51) Int. Cl.
*A61B 5/24* (2021.01)
*G06N 3/04* (2006.01)

(58) Field of Classification Search
USPC .......................................................... 706/25
See application file for complete search history.

(56) References Cited

OTHER PUBLICATIONS

Garcia et al. ("Unsupervised classification of neural spikes with a hybrid multilayer artificial neural network" 1998) (Year: 1998).*
Bausch et al. ("An Unsupervised Method for Realtime Spike Sorting" 2011) (Year: 2011).*
Preliminary Search Report as issued in French Patent Application No. 1654485, dated Feb. 8, 2017.
Zhang, B., et al., "A Neuromorphic Neural Spike Clustering Processor for Deep-Brain Sensing and Stimulation Systems," 2015 IEEE/ACM International Symposium on Lower Power Electronics and Design (ISLPED), Jul. 2015, XP055342652, pp. 91-97.
Corradi, F., et al., "A Neuromorphic Event-Based Neural Recording System for Smart Brain-Machine-Interfaces," IEEE Transactions on Biomedical Circuits and Systems, vol. 9, No. 5, Oct. 2015, XP055236096, pp. 699-709.

\* cited by examiner

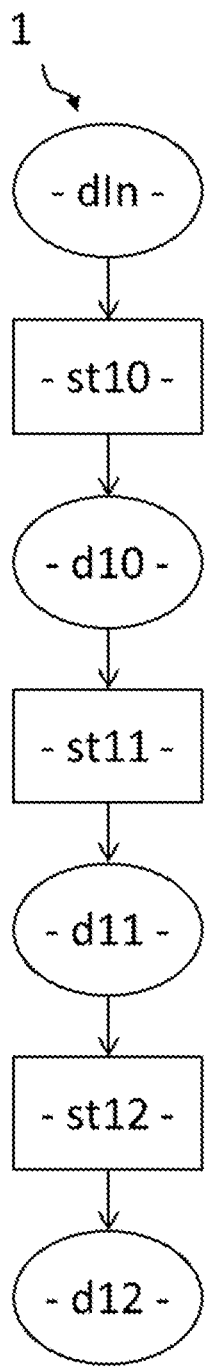
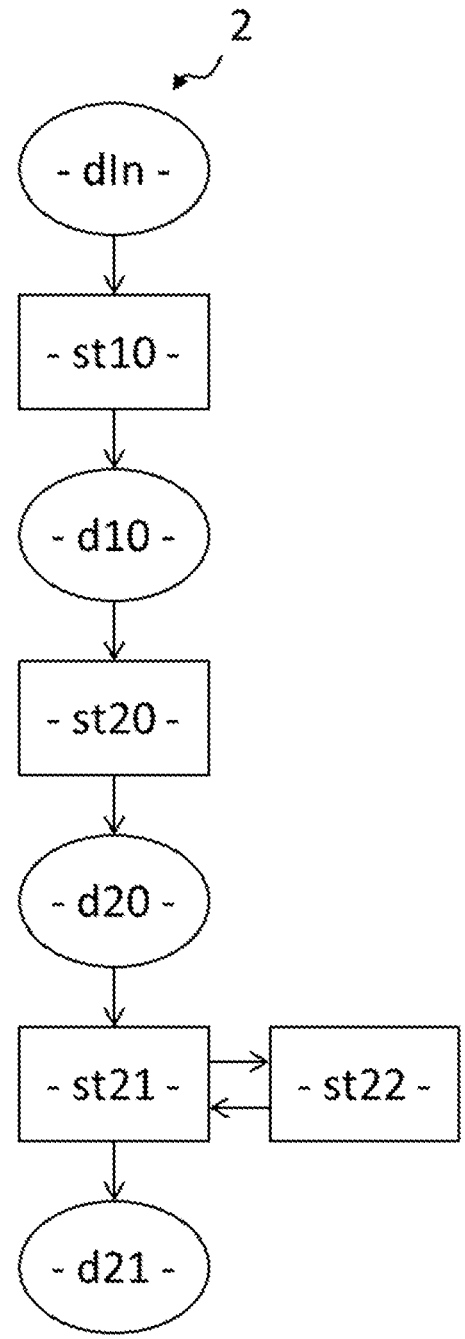
Fig. 1a  Fig. 1b

METHOD FOR UNSUPERVISED SORTING IN REAL TIME OF ACTION POTENTIALS OF A PLURALITY OF BIOLOGICAL NEURONS

CROSS-REFERENCE TO RELATED APPLICATIONS

This application claims priority to French Patent Application No. 1654485 filed May 19, 2016, the entire contents of all applications are incorporated herein by reference in their entireties.

TECHNICAL FIELD OF THE INVENTION

The technical field of the invention is that of the sorting of action potentials of biological neurons. The present invention relates to a method for unsupervised sorting in real time of action potentials of a plurality of biological neurons.

A field of application of the present invention is notably that of neuroprosthetics and brain-computer interfaces, that is to say direct communication interfaces between a brain and an external device such as a computer. A brain-computer interface exploits the electrical properties of neurons and may be designed to assist, improve or repair faulty human action functions.

TECHNOLOGICAL BACKGROUND OF THE INVENTION

In neurobiology, a microelectrode is an element of a device making it possible to measure a difference in electrical potential between two points of a biological system, for example:

between the inside of a neuron and a reference point: it is then an intracellular microelectrode, or between a point close to a neuron and a reference point: it is then an extracellular microelectrode.

The type of signal obtained by measuring the electrical field generated by a neuron from the interior of said neuron is very different from that obtained by measuring said electric field from the exterior of said neuron.

When a neuronal activity is recorded by means of an extracellular microelectrode, the potential difference measured reflects the currents passing through the membrane of the neurons situated near to said extracellular microelectrode. These membrane currents comprise:

membrane currents with rapid variations, that is to say at frequencies of the order of 1 kHz, which underlie the creation and the propagation of action potentials (or "spikes"), and membrane currents with slower variations, that is to say at frequencies in the interval ranging from 0 Hz to 500 Hz, called LFP (local field potentials), which mainly underlie synaptic activities.

By carrying out a band pass filtering of the raw signal recording the totality of the neuronal activity, it is possible to isolate the neuronal activity corresponding uniquely to action potentials. The band pass filtering is for example carried out between 300 Hz and 3 kHz when the neuronal activity linked to the action potentials is used for studying the dynamic of sets of neurons, and for brain-computer interface applications.

When a neuron sufficiently close to the tip of an extracellular microelectrode emits an action potential, the extracellular microelectrode records this action potential. The tip of an extracellular microelectrode being generally near to several neurons, the signal recorded by the extracellular microelectrode may comprise a superposition of action potentials generated by several different active neurons. A given neuron typically emits an action potential for a certain type of behavior or sensorial experience by an individual. For example, a first neuron of the motor cortex may emit an action potential for a movement of the arm towards the left whereas a second neuron of the motor cortex, neighboring the first neuron, emits for its part an action potential for a movement of the arm towards the right. It is thus very important to separate, or sort, the action potentials specific to each neuron from the raw signal recorded by an extracellular microelectrode. Such a sorting of action potentials is typically carried out by using the fact that each neuron emits on a given microelectrode action potentials having a specific form. The specific form, on a given microelectrode, of the action potentials emitted by each neuron depends notably on the geometry of the neuron and the position of the neuron with respect to the microelectrode.

In the context of brain-computer interfaces where it is sought to decode a neuronal signal to predict a behavior, such as for example a movement, better results are obtained with data of sorted action potentials than with data of unsorted action potentials. Even more precise results are also obtained when the activity of a large number of neurons is recorded. Current recording techniques make it possible to use simultaneously hundreds of microelectrodes.

Several offline methods for sorting action potentials are known, according to which the raw signal coming from the microelectrode(s) is firstly entirely recorded and stored before being processed. An offline sorting method may implement long computations or resort to the supervision of a human operator. This is not the case of a method for sorting in real time, which has to be able to process the raw signal at each instant, progressively. FIG. 1a shows a diagram of the steps of a first method 1 for sorting action potentials according to the prior art. The first method 1 comprises:

from input data dIn, a first step st10 of detection of action potentials and storage of waveforms of the detected action potentials d10;

from the waveforms of the detected action potentials d10, a second step st11 of extraction of relevant characteristics d11;

from the relevant characteristics d11, a third step st12 of clustering said relevant characteristics d11 to obtain sorted action potentials d12.

Different strategies may be used at each of these three steps. During the first step st10, the detection of the action potentials is generally carried out by a detection of overstepping of the amplitude or energy threshold of the raw signal. When an action potential is detected, its waveform is recorded. The second step st11 of extraction of relevant characteristics aims to construct the space of the characteristics of waveforms before the third step st12 of clustering. Predefined characteristics such as the amplitude, the width, the area, the wavelet coefficients or the complete waveform over 8 certain predefined time window may be used as relevant characteristics. The second step st11 may also comprise a sub-step of reduction of the dimensionality of the space of the characteristics. To do so, a conventional approach is to carry out a PCA (principal component analysis) of the matrix of characteristics, such as those of waveforms. The third step st12 then consists in sorting the action potentials by clustering them together from the extracted and, if need be, reduced characteristics. Numerous clustering algorithms exist, among which the k-means algorithm or the expectation-maximization algorithm. Nevertheless, these clustering methods generally require knowledge of the number of groups to realize. The supervision of an operator is then necessary in order to supply this input data.

Zhang et al. have recently proposed, in their article "A neuromorphic neural spike clustering processor for deep-brain sensing and stimulation systems" (ISLPED, 2015), a second method 2 for sorting action potentials by means of a network of artificial neurons implementing plasticity rules as a function of the occurrence time of the spikes, or STDP rules (spike-timing-dependent plasticity). FIG. 1b shows a diagram of the steps of the second method 2 according to the prior art, After the first step st10 of detection of the action potentials and recording of the waveforms of the detected action potentials d10, the second method 2 comprises a second step st20 according to which the waveforms d10 are encoded in the form of spikes d20, then a third step st21 according to which the spikes d20 are injected into a network of artificial neurons to obtain sorted action potentials d21. A step st22 of controlling the quality of the results obtained by the network of artificial neurons is provided. Thanks to the STDP rules, the network of artificial neurons then learns to recognize the different waveforms of the action potentials. The first step st10 of detection of action potentials and recording of the waveforms of the detected action potentials implies nevertheless a preprocessing and a storage of data outside of the neuromorphical processor implementing the network of artificial neurons.

It is desired to be able to sort in real time, at each instant, the action potentials recorded by a plurality of microelectrodes by an entirely automatic, unsupervised sorting method, and being able to be entirely implemented on a neuromorphic circuit.

SUMMARY OF THE INVENTION

The invention offers a solution to the problems evoked previously, making it possible to sort action potentials in real time and in an unsupervised manner, that is to say without return of information as a function of the result of an output layer, in other words without feedback or inverse feedback, as in the case of reinforcement learning.

One aspect of the invention relates to a method for unsupervised sorting, in real time, of action potentials of a plurality of biological neurons by means of a network of artificial neurons comprising an input layer, an intermediate layer and an output layer, each artificial neuron of the input layer being connected to a plurality of artificial neurons of the intermediate layer by a plurality of first excitatory synapses and each artificial neuron of the intermediate layer being connected to a plurality of artificial neurons of the output layer by a plurality of second excitatory synapses, at least one first or second excitatory synapse connecting a first artificial neuron to a second artificial neuron and having a weight that is modified as a function of the instants at which take place presynaptic spikes emitted by the first artificial neuron and postsynaptic spikes emitted by the second artificial neuron, method according to which:
the input layer receives an electrical signal measuring an electrical activity of a plurality of biological neurons, the electrical signal having a variable amplitude as a function of action potentials emitted by the plurality of biological neurons over time;
the input layer converts the amplitude of the electrical signal into a train of first spikes;
the input layer transmits the train of first spikes to the intermediate layer;
the intermediate layer converts the train of first spikes into a train of second spikes;
the intermediate layer transmits the train of second spikes to the output layer;
as a function of the train of second spikes, the output layer sorts each occurrence of each type of action potential present in the electrical signal.

The property is exploited according to which the presence of a given type of action potential results in a given variation of amplitude in the electrical signal.

It is thus possible to discriminate each type of action potential. Thanks to the invention, the input layer directly acquires the electrical signal measuring the electrical activity of a plurality of biological neurons. By avoiding the step of detection and encoding of the methods of the prior art, the method for sorting action potentials according to one aspect of the invention may advantageously be entirely implemented on a neuromorphic circuit, without requiring pre-processing and/or storage external to this neuromorphic circuit.

In the present document, "the output layer sorts each occurrence of each type of action potential present in the electrical signal" is taken to mean the fact that, for each type of action potential, the output layer carries out an act that is specific to said type of action potential and which is identical for each occurrence of said type of action potential.

Apart from the characteristics that have been evoked in the preceding paragraph, the sorting method according to one aspect of the invention may have one or more additional characteristics among the following, considered individually or according to all technically possible combinations thereof.

As a function of the train of second spikes the output layer sorts each occurrence of each type of action potential present in the electrical signal by activating at the most a single group of artificial neurons of the output layer for each occurrence of an action potential in the electrical signal, each group of artificial neurons of the output layer comprising at least one artificial neuron of the output layer and being associated with a single type of action potential and each type of action potential being associated with a single group of artificial neurons of the output layer. Each group of artificial neurons of the output layer preferentially comprises a single artificial neuron of the output layer. Alternatively, each group of artificial neurons of the output layer may comprise several artificial neurons of the output layer, for example in order to enable a redundancy.

The input layer is a matrix of artificial neurons having:
Na lines, the number Na of lines being chosen as a function of a range of values in which the amplitude of the electrical signal is variable, in such a way that the artificial neurons of a same line are activated for a same amplitude value of the electrical signal, and
Nt columns, the number Nt of columns being chosen as a function of a time frame for observing the electrical signal, in such a way that the artificial neurons of a same column receive the electrical signal at a same given instant;
and at each instant $t_n = n*dt$, with n a natural integer and dt a time step:
a first column $C_0$ of artificial neurons receives the electrical signal, and
as a function of the amplitude value of the electrical signal received, at least one artificial neuron of the first column $C_0$ emits a spike that is transmitted to the intermediate layer.

The method for sorting action potentials according to one aspect of the invention carries out a storage of information uniquely over a duration corresponding to the time frame for observing the electrical signal. The time frame for observing the electrical signal is typically of the order of the duration of an action potential.

The time frame for observing the electrical signal is thus generally comprised between 0.1 ms and 5 ms, and preferentially comprised between 0.5 ms and 1 ms.

A margin is defined around each amplitude value of the electrical signal received in such a way that, at each instant $t_n = n*dt$:
- the first column $C_0$ of artificial neurons receives the electrical signal, and
- as a function of the amplitude value of the electrical signal received and of the margin defined around said amplitude value, at least two artificial neurons of the first column $C_0$ each emit a spike, each spike being transmitted to the intermediate layer.

Thanks to this margin, advantageously a sensitivity interval is defined for each artificial neuron of the input layer. The union of the sensitivity intervals of all the artificial neurons of the input layer typically covers the range of values in which the amplitude of the signal is variable. There exists an overlap between the sensitivity intervals in such a way that for each given amplitude value of the electrical signal received, several artificial neurons of the input layer react by each emitting a spike. In this way, the robustness of the method according to one aspect of the invention is increased.

The number Nt of columns of the input layer being strictly greater than 1, at each instant $t_k = t_n + k*dt'$ and for each column $C_k$ of artificial neurons, with dt' a second time step and k a natural integer such that $1 \leq k \leq Nt-1$, each artificial neuron of same line as an artificial neuron of the first column $C_0$ having emitted a spike at the instant $t_n$, emits in its turn a spike that is transmitted to the intermediate layer.

This makes it possible that the electrical signal is received uniquely by the artificial neurons of the first column $C_0$, and not necessarily by all of the artificial neurons of the input layer. The information of amplitude variation of the electrical signal, initially received by the first column $C_0$ of artificial neurons, may be transmitted little by little to the other columns of artificial neurons of the input layer. Alternatively, the first column $C_0$ of artificial neurons transforming the information of amplitude variation of the electrical signal that it receives into a spike emission information by one or more lines of artificial neurons, this spike emission information may be transmitted little by little to the other columns of the input layer. The second time step dt' may be identical to the time step dt or distinct from the time step dt.

Each artificial neuron of the input layer is connected to a plurality of artificial neurons of the intermediate layer by a plurality of first excitatory synapses in such a way that a spike emitted by said artificial neuron of the input layer is transmitted to the plurality of artificial neurons of the intermediate layer by the plurality of first excitatory synapses.

Each artificial neuron of the intermediate layer is connected to a plurality of artificial neurons of the output layer by a plurality of second excitatory synapses in such a way that a spike emitted by said artificial neuron of the intermediate layer is transmitted to the plurality of artificial neurons of the output layer by the plurality of second excitatory synapses. Each excitatory synapse has a weight, each artificial neuron of the intermediate layer and each artificial neuron of the output layer have a potential having initially a value designated "rest value".

When an excitatory synapse transmits a spike to an artificial neuron of the intermediate layer or of the output layer, the potential of said artificial neuron increases proportionally to the weight of said first excitatory synapse. When the potential of an artificial neuron of the intermediate layer or of the output layer exceeds a threshold value, said artificial neuron emits a spike and its potential is lowered to a reset value or alternatively said artificial neuron is prevented from re-emitting a spike for a refractory period. In the absence of spike at the input of an artificial neuron of the intermediate layer or of the output layer and when this neuron does not itself emit a spike, the potential of said neuron returns to its rest value in a characteristic time $T_m$.

This mechanism makes it possible to avoid the artificial neurons from emitting spikes in a non-specific manner.

The manner in which the potential of each artificial neuron increases or returns to its rest value is typically determined by a LIF (leaky-integrate-and-fire) model. The weight of a synapse is also called "synaptic weight". The potential of an artificial neuron is also called "membrane potential" or "transmembrane potential".

The weight of each excitatory synapse is modified as a function of a predefined time window:
- for a given excitatory synapse, when the predefined time window comprises a presynaptic spike and a postsynaptic spike, the weight of this excitatory synapse is increased;
- for a given excitatory synapse, when the predefined time window comprises a postsynaptic spike only, the weight of this excitatory synapse is decreased;
- for a given excitatory synapse, when the predefined time window comprises a presynaptic spike only, the weight of this excitatory synapse remains unchanged.

For a given excitatory synapse connecting a first artificial neuron to a second artificial neuron, "presynaptic spike" is taken to mean a spike emitted by the first artificial neuron and transmitted by said excitatory synapse to the second artificial neuron and "postsynaptic spike" is taken to mean a spike emitted by the second artificial neuron.

This mechanism contributes to the learning, by the network of artificial neurons, of each waveform of action potential.

Each artificial neuron of the input layer is connected to a plurality of artificial neurons of the intermediate layer by a plurality of first excitatory synapses in such a way that a spike emitted by an artificial neuron of the input layer is transmitted to the plurality of artificial neurons of the intermediate layer. For a first given excitatory synapse connecting an artificial neuron of the input layer to an artificial neuron of the intermediate layer, "presynaptic artificial neuron" is taken to mean the artificial neuron of the input layer and "postsynaptic artificial neuron" is taken to mean the artificial neuron of the intermediate layer.

According to a first embodiment, each first excitatory synapse has a weight allotted a synaptic coefficient $P_{rel}$ such that $0 \leq P_{rel} \leq 1$, the synaptic coefficient $P_{rel}$ decreasing when the presynaptic artificial neuron emits a spike, and the synaptic coefficient $P_{rel}$ increasing towards 1 otherwise with a characteristic time $T_{stp}$. Each postsynaptic artificial neuron receiving a spike via a first excitatory synapse is excited proportionally to the product of the synaptic coefficient $P_{rel}$ and the weight of said first excitatory synapse. This characteristic, designated "short term plasticity" between the input layer and the intermediate layer, advantageously makes it possible to contribute to filtering the noise of the electrical signal received by the input layer in order that the artificial neurons of the intermediate layer are not activated by the noise, and thus that the artificial neurons of the output layer are not activated by the noise.

Alternatively to the characteristic of short term plasticity between the input layer and the intermediate layer according to the first embodiment, a characteristic short term plasticity between the intermediate layer and the output layer may be provided in order that the artificial neurons of the output layer are not activated by noise. Each artificial neuron of the intermediate layer is connected to a plurality of artificial neurons of the output layer by a plurality of second excitatory synapses in such a way that a spike emitted by an artificial neuron of the intermediate layer is transmitted to the plurality of artificial neurons of the output layer. For a second given excitatory synapse connecting an artificial neuron of the intermediate layer to an artificial neuron of the output layer, "presynaptic artificial neuron" is taken to mean the artificial neuron of the intermediate layer and "postsynaptic artificial neuron" is taken to mean the artificial neuron of the output layer. Each second excitatory synapse has a weight allotted a synaptic coefficient $P_{rel}$ such that $0 \leq P_{rel} \leq 1$, the synaptic coefficient $P_{rel}$ decreasing when the presynaptic artificial neuron emits a spike, and the synaptic coefficient $P_{rel}$ increasing towards 1 otherwise with a characteristic time $T_{stp}$. Each postsynaptic artificial neuron receiving a spike via a second excitatory synapse is excited proportionally to the product of the synaptic coefficient $P_{rel}$ and the weight of said second excitatory synapse.

It is possible to provide both the characteristic of short term plasticity between the input layer and the intermediate layer, and the characteristic of short term plasticity between the intermediate layer and the output layer.

According to a second embodiment, the network of artificial neurons also comprises at least one artificial detection neuron, each artificial neuron of the input layer being connected to the artificial detection neuron by a first excitatory detection synapse, and the artificial detection neuron being connected to a plurality of artificial neurons of the intermediate layer by a plurality of second excitatory detection synapses. According to the second embodiment, each first excitatory detection synapse has a weight allotted a synaptic coefficient $P_{rel}$ such that $0 \leq P_{rel} \leq 1$, the synaptic coefficient $P_{rel}$, decreasing when the presynaptic artificial neuron emits a spike and the synaptic coefficient $P_{rel}$ increasing towards 1 otherwise with a characteristic time $T_{stp}$, and the artificial detection neuron receiving a spike via a first excitatory detection synapse is excited proportionally to the product of the synaptic coefficient $P_{rel}$ and the weight of said first excitatory detection synapse. According to the second embodiment, a short term plasticity rule is thus implemented uniquely between the artificial neurons of the input layer and the artificial detection neuron, and not between the artificial neurons of the input layer and the artificial neurons of the intermediate layer. The binary detection function is thus separated, that is to say "presence" or "absence", from the action potentials on the one hand, and the discrimination function of the action potentials present on the other hand: the artificial detection neuron ensures the binary detection function thanks to the short term plasticity rule whereas the artificial neurons of the intermediate layer ensure the discrimination function thanks to a STDP rule. The artificial detection neuron emits spikes when it detects the presence of an action potential in the train of first spikes emitted by the artificial neurons of the input layer and transmitted via the first excitatory detection synapses, and do not emit a spike otherwise. The spikes emitted by the artificial detection neuron are transmitted to the artificial neurons of the intermediate layer via the second excitatory detection synapses.

Thus, as a function of the spikes that it emits, the artificial detection neuron modulates the activity of the artificial neurons of the intermediate layer.

According to an improvement of the second embodiment, the network of artificial neurons comprises a recurrent excitatory synapse, from the artificial detection neuron towards itself. Thus, once the spike emission threshold of the artificial detection neuron is overstepped, the artificial detection neuron receives an additional excitation by the recurrent excitatory synapse. The excitation coming from the artificial neurons of the input layer thus has to descend below a threshold less than the preceding emission threshold in order that the artificial detection neuron ceases to emit spikes, according to a hysteresis mechanism. This makes it possible to ensure a continuity in the detection, even in the case where the form of the action potential provisionally passes by values close to zero. The detection function is thus improved.

According to an improvement of the first or the second embodiment, an artificial neuron of the intermediate layer or of the output layer may receive a spike of an artificial neuron of the preceding layer both via an excitatory synapse and via an inhibitory synapse, each synapse obeying an STDP rule. The STDP rule of the excitatory synapse is reversed with respect to the STDP rule of the inhibitory synapse, in such a way that when the weight of the excitatory synapse increases, that of the inhibitory synapse decreases, and conversely when the weight of the excitatory synapse decreases, that of the inhibitory synapse increases. Thus, the sum of the weights of the excitatory synapse and of the inhibitory synapse is not cancelled out—except if each of the two weights is zero, because when the weight of the excitatory synapse is high, that of the inhibitory synapse is low and vice versa. Using negative contributions through inhibitory synapses in addition to the positive contributions of the excitatory synapses makes it possible to improve the recognition of the different patterns of action potentials.

According to another improvement of the first or the second embodiment, an artificial neuron of the intermediate layer or of the output layer may receive a same spike of an artificial neuron of the preceding layer via a plurality of excitatory synapses each having a different transmission delay and/or via a plurality of inhibitory synapses each having a different transmission delay, each synapse obeying a STDP law. For example, an artificial neuron may thus receive simultaneously:
 a spike coming from a first artificial neuron of the preceding layer via a synapse having a short delay, and
 a spike coming from a second artificial neuron of the preceding layer via a synapse having a long delay.

In this example, there is then an information on the fact that the second artificial neuron has emitted a spike before the first artificial neuron. Generally speaking, this improvement enables a layer of artificial neurons to have an information on the relative instants of emission of a spike by the artificial neurons of the preceding layer. The precision of the sorting method according to one aspect of the invention is thus improved, enabling it to differentiate a larger number of patterns.

According to an improvement of the second embodiment, the artificial detection neuron is connected to a plurality of artificial neurons of the output layer by a plurality of second inhibitory detection synapses: the spikes of the artificial detection neuron, transmitted to the artificial neurons of the output layer via the plurality of second inhibitory detection synapses, force the artificial neurons of the output layer to reach the end of an action potential before emitting a spike.

This thus contributes to controlling the instant of emission of a spike by the artificial neurons of the output layer. In particular, this contributes to avoiding that an artificial neuron of the output layer emits a spike before the end of an action potential present in the signal. In fact, if an artificial neuron of the output layer emits a spike before the end of an action potential, it risks missing important information to sort the action potential in question, as is for example the case when two types of action potentials begin in the same way but finish differently. According to this improvement, the artificial neurons of the output layer are inhibited by the artificial detection neuron throughout the duration of an action potential. It is thus ensured that the output artificial neurons can be excited after the end of the action potential, for example by introducing a transmission delay in the synaptic connections between the intermediate layer and the output layer. In fact, since the artificial neurons of the output layer are inhibited for the duration of an action potential, whereas the artificial neurons of the intermediate layer only emit spikes for the duration of an action potential, if it is not ensured that the artificial neurons of the output layer can be excited after the end of the action potential, they will not a priori ever be excited.

Each artificial neuron of the intermediate layer is connected to all of the other artificial neurons of the intermediate layer by a plurality of first inhibitory synapses in such a way that a spike emitted by said artificial neuron of the intermediate layer is transmitted to all of the other artificial neurons of the intermediate layer by the plurality of first inhibitory synapses. Each artificial neuron of the output layer is connected to all of the other artificial neurons of the output layer by a plurality of second inhibitory synapses in such a way that a spike emitted by said artificial neuron of the output layer is transmitted to all of the other artificial neurons of the output layer by the plurality of second inhibitory synapses. According to a first alternative, when an inhibitory synapse transmits a spike to an artificial neuron of the intermediate layer or of the output layer, said artificial neuron is prevented from emitting a spike for a predefined duration designated "inhibition period". According to a second alternative, when an inhibitory synapse transmits a spike to an artificial neuron of the intermediate layer or of the output layer, the potential of said artificial neuron is decreased proportionally to the weight of said inhibitory synapse. The use of an inhibition period, in the first alternative, makes it possible to manage the time between two successive spikes more precisely than in the second alternative. The reduction in potential used in the second alternative enables greater flexibility: for example, if two action potentials arrive simultaneously or nearly simultaneously, the output layer could emit two spikes corresponding to these action potentials despite the inhibition. According to a third alternative combining the first and second alternatives, when an inhibitory synapse transmits a spike to an artificial neuron of the intermediate layer or of the output layer, said artificial neuron is prevented from emitting a spike for a predefined duration designated "inhibition period" and the potential of said artificial neuron is decreased proportionally to the weight of said inhibitory synapse.

This "winner takes all" type mechanism advantageously contributes to preventing several artificial neurons from learning the same action potential waveform. In the case where the output layer activates, for each occurrence of an action potential in the electrical signal, a single group of artificial neurons of the output layer comprising several artificial neurons of the output layer, there is advantageously no lateral inhibition between the artificial neurons of a same group.

A plurality of second excitatory synapses connects each artificial neuron of the intermediate layer to a plurality of artificial neurons of the output layer, each second excitatory synapse having a weight. For each second excitatory synapse, when an artificial neuron of the output layer receives, in a predefined time window, a spike transmitted by said second excitatory synapse and a spike transmitted by a second inhibitory synapse, then the weight of said second excitatory synapse is decreased. For each second excitatory synapse, when an artificial neuron of the output layer receives, in the predefined time window, a spike transmitted by said second excitatory synapse and no spike transmitted by a second inhibitory synapse, then the weight of said second excitatory synapse is increased.

This mechanism, herein called inhibition induced plasticity, advantageously contributes to preventing several artificial neurons from learning the same action potential waveform and thus increases learning precision. The inhibition induced plasticity mechanism is advantageously combined with the "winner takes all" type mechanism described previously.

Each artificial neuron of the output layer has a potential; each artificial neuron of the output layer emits a spike when its potential exceeds a threshold value. The threshold value of each artificial neuron of the output layer emitting a spike at an instant t is increased proportionally to the number of spikes received by said artificial neuron in a time window around the instant t. The threshold value Th of each artificial neuron of the output layer emitting a spike at an instant t1 is decreased in such a way that:

$$Th(t2)=\alpha*Th(t1)$$

with $Th(t1)$ the threshold value at the instant t1, $Th(t2)$ the threshold value at an instant t2 later than t1 and $\alpha$ a real number such that $0<\alpha<1$.

The above mechanism introduces a plasticity on the threshold value of each artificial neuron of the output layer, called intrinsic plasticity. Advantageously the robustness of the method according to one aspect of the invention to potential variations, from one waveform to another, of the number of spikes transmitted to the output layer is thus increased. During an initialization period, or learning period, of the method for sorting action potentials according to one aspect of the invention, and although a mechanism of "winner takes all" type is implemented, it may happen that several artificial neurons of the output layer emit, one after the other, spikes for a same action potential if their threshold is poorly suited. The intrinsic plasticity mechanism that has been described has the advantage of not depending on the precise instant t of emission of each spike by an artificial neuron of the output layer, thanks to the time window that surrounds the instant t. This makes it possible to improve learning by contributing to guaranteeing that an action potential activates a single group of neurons of the output layer.

Alternatively, another intrinsic plasticity mechanism may be used. The threshold value of each artificial neuron of the output layer emitting a spike at an instant t is decreased proportionally to the number of spikes received by said artificial neuron in a first time window before the instant t. The threshold value of each artificial neuron of the output layer emitting a spike at an instant t is increased proportionally to the number of spikes received by said artificial neuron in a second time window after the instant t.

The above alternative mechanism also advantageously introduces a plasticity on the threshold value of each artificial neuron of the output layer in order to increase the robustness of the method according to one aspect of the invention to potential variations, from one waveform to another, of the number of spikes transmitted to the output layer.

When an intrinsic plasticity is introduced on the threshold value of each artificial neuron of the output layer, according to one or the other of the two alternatives that have been described, preferentially, the "winner takes all" type mechanism and the mechanism of inhibition induced plasticity between the intermediate layer and the output layer are also implemented. This thus contributes to guaranteeing that a given action potential is only learnt by a single artificial neuron of the output layer, despite the variability introduced on the threshold value of each artificial neuron of the output layer.

The network of artificial neurons comprises the input layer, the intermediate layer, a second intermediate layer and the output layer, and:
 the input layer transmits the train of first spikes to the intermediate layer and to the second intermediate layer;
 the second intermediate layer converts the train of first spikes into a second train of second spikes;
 the second intermediate layer transmits the second train of second spikes to the output layer;
 as a function of the train of second spikes and the second train of second spikes, the output layer sorts each occurrence of each type of action potential present in the electrical signal.

In this configuration, a double processing of the train of first spikes is carried out in parallel by the first and second intermediate layers.

This configuration advantageously makes it possible to increase the robustness of the method according to one aspect of the invention. The weight of each excitatory synapse connecting an artificial neuron of the input layer to an artificial neuron of the intermediate layer or to an artificial neuron of the second intermediate layer is typically initialized randomly. Consequently, the train of second spikes at the output of the intermediate layer is a priori different from the second train of second spikes at the output of the second intermediate layer. Each intermediate layer is thus likely to have, in certain cases, less good results than the other. It is on the other hand not very probable that two different intermediate layers commit the same errors. Which is why combining two intermediate layers makes it possible to increase the performances.

The network of artificial neurons comprises the input layer, the intermediate layer, a second intermediate layer and the output layer, and:
 a part of the input layer transmits a second train of first spikes to the second intermediate layer;
 the second intermediate layer converts the second train of first spikes into a second train of second spikes;
 the second intermediate layer transmits the second train of second spikes to the output layer;
 as a function of the train of second spikes and the second train of second spikes, the output layer sorts each occurrence of each type of action potential present in the electrical signal.

In this configuration, the input layer transmits the train of first spikes to the intermediate layer whereas the part of the input layer transmits the second train of first spikes to the second intermediate layer: the second train of first spikes is a part of the train of first spikes. In other words, the second train of first spikes is included in the train of first spikes.

The input layer being a matrix of artificial neurons, the part of the input layer may comprise the same number of lines as the input layer and a number of columns less than that of the input layer. In this case, the part of the input layer makes it possible to take specifically into account a small time frame for observing the electrical signal within the time frame for observing the input layer. The choice of the size of the observation time frame has an influence on the results obtained. The larger the observation time frame, the less errors due to noise are suffered. However, a too large observation time frame, that is to say typically an observation time frame larger than the duration of an action potential, contains a lot of insignificant signal and does not make it possible to obtain a relevant result.

Choosing several observation time frames of different sizes thus makes it possible to make the best of each size, without knowing precisely the ideal size of an observation time frame—which is not necessarily the same for the different action potentials. Alternatively, the part of the input layer may comprise the same number of columns as the input layer and a number of lines less than that of the input layer.

Alternatively, the network of artificial neurons comprises the input layer, a second input layer, the intermediate layer and the output layer, and:
 the second input layer receives a second electrical signal measuring an electrical activity of a second plurality of biological neurons, the second electrical signal having a variable amplitude as a function of action potentials emitted by the second plurality of biological neurons over time;
 the second input layer converts the amplitude of the second electrical signal into a second train of first spikes;
 the second input layer transmits the second train of first spikes to the intermediate layer;
 the intermediate layer converts the train of first spikes and the second train of first spikes into a train of second spikes.

The second electrical signal may be different from the first electrical signal or identical to the first electrical signal. When the second electrical signal is different from the first electrical signal, the second electrical signal may for example be the derivative of the first electrical signal, or the first and second electrical signals may come from two distinct extracellular microelectrodes. This configuration has a particular interest when several extracellular microelectrodes close to each other are used to record the electrical activity of the same biological neurons. The first electrical signal is for example recorded by a first extracellular microelectrode and the second electrical signal is for example recorded by a second extracellular microelectrode near to the first extracellular electrode; the first and second extracellular microelectrodes recording the electrical activity of common biological neurons.

The artificial neurons of the input layer having a certain sensitivity interval, the artificial neurons of the second input layer advantageously have another sensitivity interval, distinct from the sensitivity interval of the artificial neurons of the input layer. In fact, each sensitivity interval is preferentially chosen as a function of the noise level.

In particular, each sensitivity interval is preferentially chosen substantially equal to three times the noise level. But this assumes knowing a priori the noise level.

The network of artificial neurons comprises the input layer, a second input layer, the intermediate layer, a second intermediate layer and the output layer, and:
- the second input layer receives a second electrical signal measuring an electrical activity of a second plurality of biological neurons, the second electrical signal having a variable amplitude as a function of action potentials emitted by the second plurality of biological neurons over time;
- the second input layer converts the amplitude of the second electrical signal into a second train of first spikes;
- the second input layer transmits the second train of first spikes to the second intermediate layer;
- the second intermediate layer converts the second train of first spikes into a second train of second spikes;
- the second intermediate layer transmits the second train of second spikes so to the output layer;
- as a function of the train of second spikes and the second train of second spikes, the output layer sorts each occurrence of each type of action potential present in the electrical signal.

The second electrical signal may be different from the first electrical signal or identical to the first electrical signal.

Compared to the preceding configuration where several input layers are connected to a single intermediate layer, this configuration according to which each input layer is connected to its own intermediate layer advantageously makes it possible that each intermediate layer has less patterns, or waveforms, to learn: the robustness and the performances of the network of artificial neurons are thus increased.

Another aspect of the invention relates to a network of artificial neurons for the implementation of a method for unsupervised sorting, in real time, of action potentials of a plurality of biological neurons, the network of artificial neurons comprising:
- an input layer for the reception of an electrical signal having a variable amplitude as a function of action potentials emitted by the plurality of biological neurons over time, the conversion of the electrical signal into a train of first spikes and the transmission of the train of first spikes to an intermediate layer;
- said intermediate layer for the conversion of the train of first spikes into a train of second spikes and the transmission of the train of second spikes to an output layer;
- said output layer for the sorting, as a function of the train of second spikes, of each occurrence of each type of action potential present in the electrical signal;
- each artificial neuron of the input layer being connected to a plurality of artificial neurons of the intermediate layer by a plurality of first excitatory synapses and each artificial neuron of the intermediate layer being connected to a plurality of artificial neurons of the output layer by a plurality of second excitatory synapses, each first or second excitatory synapse connecting a first artificial neuron to a second artificial neuron and having a weight that is modified as a function of the instants at which take place presynaptic spikes emitted by the first artificial neuron and postsynaptic spikes emitted by the second artificial neuron.

The invention and its different applications will be better understood on reading the description that follows and by examining the figures that accompany it.

BRIEF DESCRIPTION OF THE FIGURES

The figures are presented for indicative purposes and in no way limit the invention.

FIG. 1a shows a diagram of the steps of a first method for supervised and offline sorting of action potentials according to the prior art.

FIG. 1b shows a diagram of the steps of a second method for offline sorting of action potentials according to the prior art.

FIG. 5 schematically shows a second network of artificial neurons for the implementation of the method of FIG. 2a.

FIG. 6 schematically shows a third network of artificial neurons for the implementation of the method of FIG. 2a.

FIG. 7 schematically shows a fourth network of artificial neurons for the implementation of the method of FIG. 2a.

FIG. 8 schematically shows a fifth network of artificial neurons for the implementation of the method of FIG. 2a.

DETAILED DESCRIPTION OF AT LEAST ONE EMBODIMENT OF THE INVENTION

Unless stated otherwise, a same element appearing in the different figures has a single reference.

In the present application, the terms "synapse" and "artificial synapse" are employed indiscriminately. In the case of a synapse connecting a first artificial neuron to a second artificial neuron:
- the first artificial neuron is also called "presynaptic neuron", vis-à-vis said synapse, and
- the second artificial neuron is also called "postsynaptic neuron", vis-à-vis said synapse.

When the first neuron emits a spike that is transmitted to the second artificial neuron, this spike is also called "presynaptic spike", vis-à-vis the second artificial neuron. When the second artificial neuron emits a spike, this spike is also called "postsynaptic spike", vis-à-vis the second artificial neuron.

FIGS. 1a and 1b have been described in the technological background of the invention.

Figure 2A:
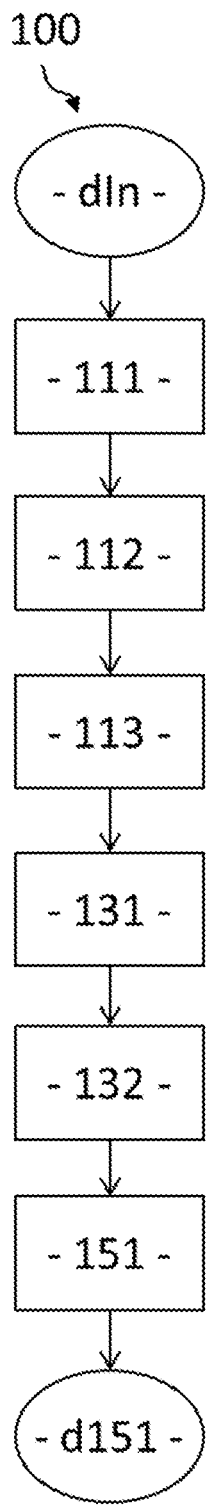
FIG. 2a shows a diagram of the steps of a method according to one aspect of the invention for unsupervised sorting, in real time, of action potentials of a plurality of biological neurons by means of a network of artificial neurons.
Figure 2B:
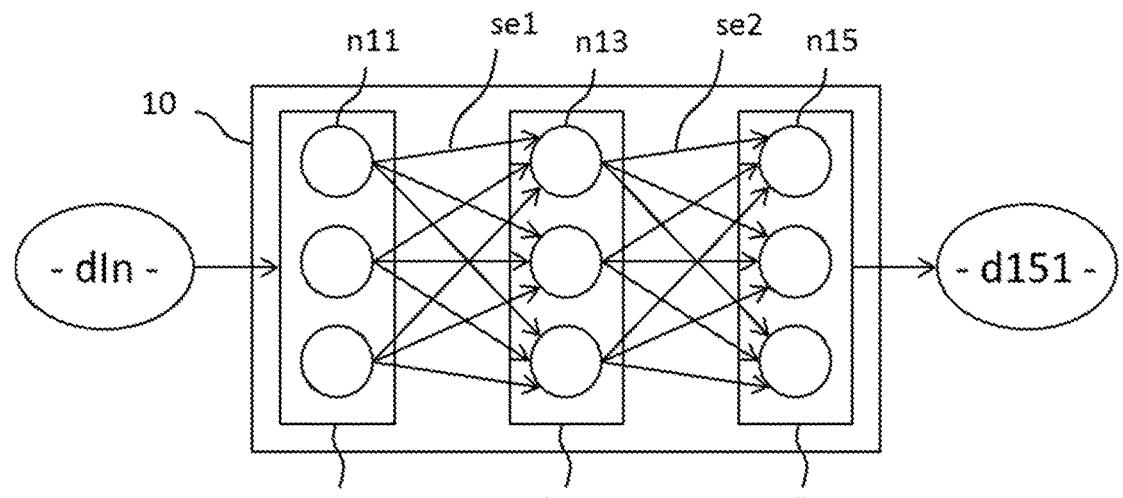
FIG. 2b schematically shows a first network of artificial neurons according to a first embodiment for the implementation of the method of FIG. 2a, the first network of artificial neurons according to the first embodiment comprising an input layer, an intermediate layer and an output layer.
Figure 2C:
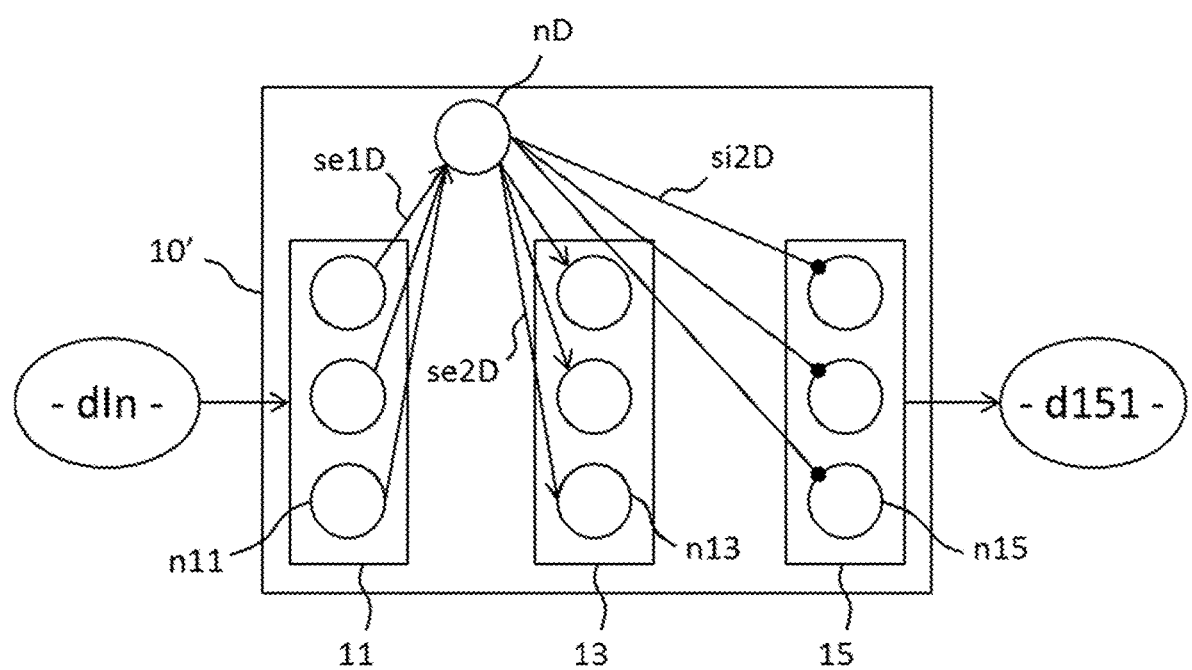
FIG. 2c schematically shows a first network of artificial neurons according to a second embodiment for the implementation of the method of FIG. 2a, the first network of artificial neurons according to the second embodiment further comprising an artificial detection neuron.

FIG. 2a shows a diagram of the steps of a method 100 according to one aspect of the invention for unsupervised sorting, in real time, of action potentials of a plurality of biological neurons by means of a network of artificial neurons. FIG. 2b schematically shows a first network of artificial neurons 10 according to a first embodiment, for the implementation of the method 100. FIG. 2c schematically shows a first network of artificial neurons 10' according to a second embodiment, for the implementation of the method 100.

FIGS. 2a, 2b and 2c are described jointly.

The first network of artificial neurons 10, 10' according to the first or the second embodiment comprises:
- an input layer 11 comprising a plurality of artificial neurons n11,
- an intermediate layer 13 comprising a plurality of artificial neurons n13, and
- an output layer 15 comprising a plurality of artificial neurons n15.

According to an embodiment, designated "all-to-all", a plurality of first excitatory synapses se1 connects each artificial neuron of the input layer n11 to the plurality of artificial neurons of the intermediate layer n13. A plurality of second excitatory synapses se2 connects each artificial neuron of the intermediate layer n13 to the plurality of artificial neurons of the output layer n15. In other words:
- each artificial neuron of the intermediate layer n13 receives a first excitatory synapse se1 coming from each artificial neuron of the input layer n11, and
- each artificial neuron of the intermediate layer n13 sends a second excitatory synapse se2 to each artificial neuron of the output layer n15.

Alternatively to an "all-to-all" connection between the artificial neurons n11 of the input layer and the artificial neurons n13 of the intermediate layer on the one hand, and between the artificial neurons n13 of the intermediate layer and the artificial neurons n15 of the output layer on the other hand, one or more partial connections may be envisaged. For example, one or more artificial neurons n11 of the input layer may only be connected to a part of the artificial neurons n13 of the intermediate layer. Similarly, one or more artificial neurons n13 of the intermediate layer may only be connected to a part of the artificial neurons n15 of the output layer.

According to the embodiment generally described in the present application, all the excitatory synapses of the first network of artificial neurons go in the same direction (feedforward excitation), to be specific: from the input layer 11 to the output layer 15. A network of artificial neurons, designated "recurrent", may alternatively be used in which certain excitatory synapses go backwards, from the output layer to the input layer.

The first network of artificial neurons 10' according to the second embodiment, illustrated in FIG. 2c, further comprises an artificial detection neuron nD. For the sake of clarity, the first and second excitatory synapses se1, se2 are not represented in FIG. 2c. Each artificial neuron n11 of the input layer is connected to the artificial detection neuron nD via a first excitatory detection synapse se1D, and the artificial detection neuron nD is connected to each artificial neuron n13 of the intermediate layer via a plurality of second excitatory detection synapses se2D. Alternatively, only a part of the artificial neurons n11 of the input layer could be connected to the artificial detection neuron nD, and/or the artificial detection neuron nD could just be connected to a part only of the artificial neurons n13 of the intermediate layer.

According to an improvement of the first network of artificial neurons 10' according to the second embodiment, the artificial detection neuron nD is connected to each artificial neuron n15 of the output layer by a second inhibitory detection synapse si2D.

According to step 111 of the method 100 for unsupervised sorting, in real time, of action potentials of a plurality of biological neurons, the input layer 11 receives an electrical signal dIn. The electrical signal dIn measures an electrical activity of a plurality of biological neurons and has a variable amplitude as a function of action potentials emitted by the plurality of biological neurons over time.

According to step 112 of the method 100, the input layer 11 next converts the amplitude of the electrical signal dIn into a train of first spikes. The train of first spikes comprises all the spikes that are emitted by the artificial neurons of the input layer n11.

After step 112, the method 100 comprises a step 113 according to which the input layer 11 transmits the train of first spikes to the intermediate layer 13 via the plurality of first excitatory synapses se1.

The intermediate layer 13 then converts the train of first spikes into a train of second spikes, according to step 131 of the method 100, then the train of second spikes is transmitted to the output layer 15 via the plurality of second excitatory synapses se2 during a step 132 of the method 100. The train of second spikes comprises all the spikes that are emitted by the artificial neurons of the intermediate layer n13.

Finally, in step 151 of the method 100, the output layer 15 sorts each occurrence of each type of action potential present in the electrical signal dIn, as a function of the train of second spikes by activating at the most a single group of artificial neurons of the output layer n15 for each occurrence of an action potential in the electrical signal dIn, each group of artificial neurons of the output layer n15 being associated with a single type of action potential and each type of action potential being associated with a single group of artificial neurons of the output layer. A group of artificial neurons may comprise several artificial neurons or instead, preferentially, a single artificial neuron.

Figure 3A:
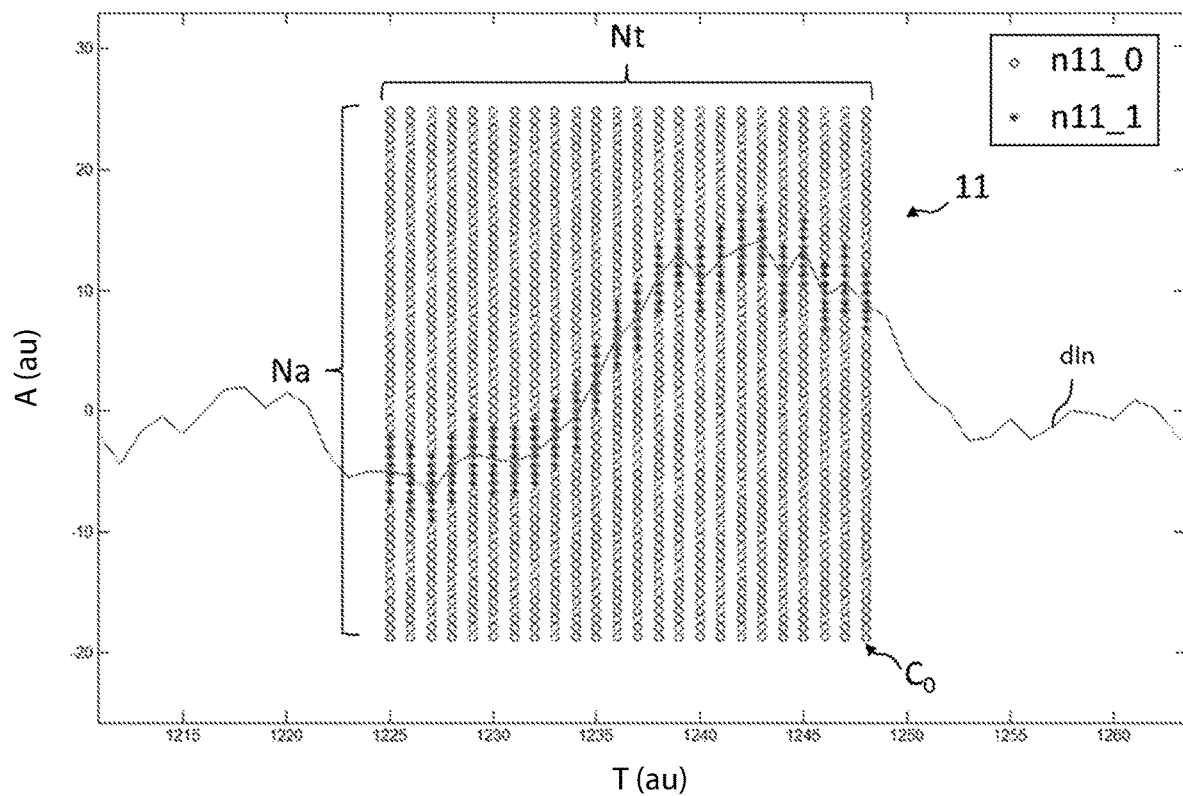
FIG. 3a schematically shows the input layer of the first network of artificial neurons of FIG. 2b receiving an electrical signal and converting the amplitude of the electrical signal into a train of first spikes.
Figure 3B:
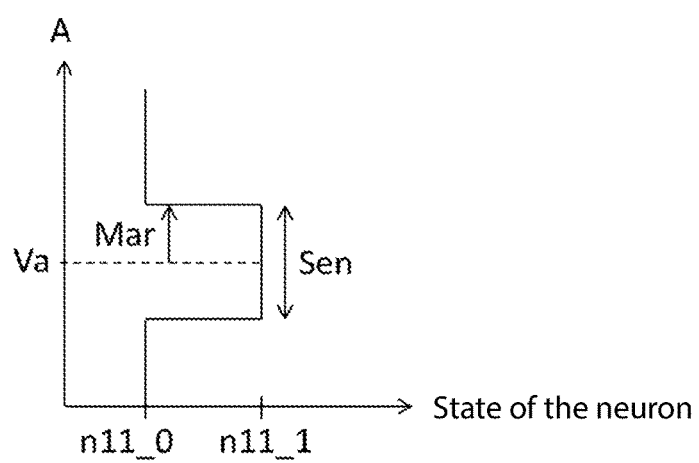
FIG. 3b schematically illustrates the definition of a margin around an amplitude value to obtain a sensitivity interval of an artificial neuron of the input layer of the first network of artificial neurons of FIG. 2b.
Figure 3C:
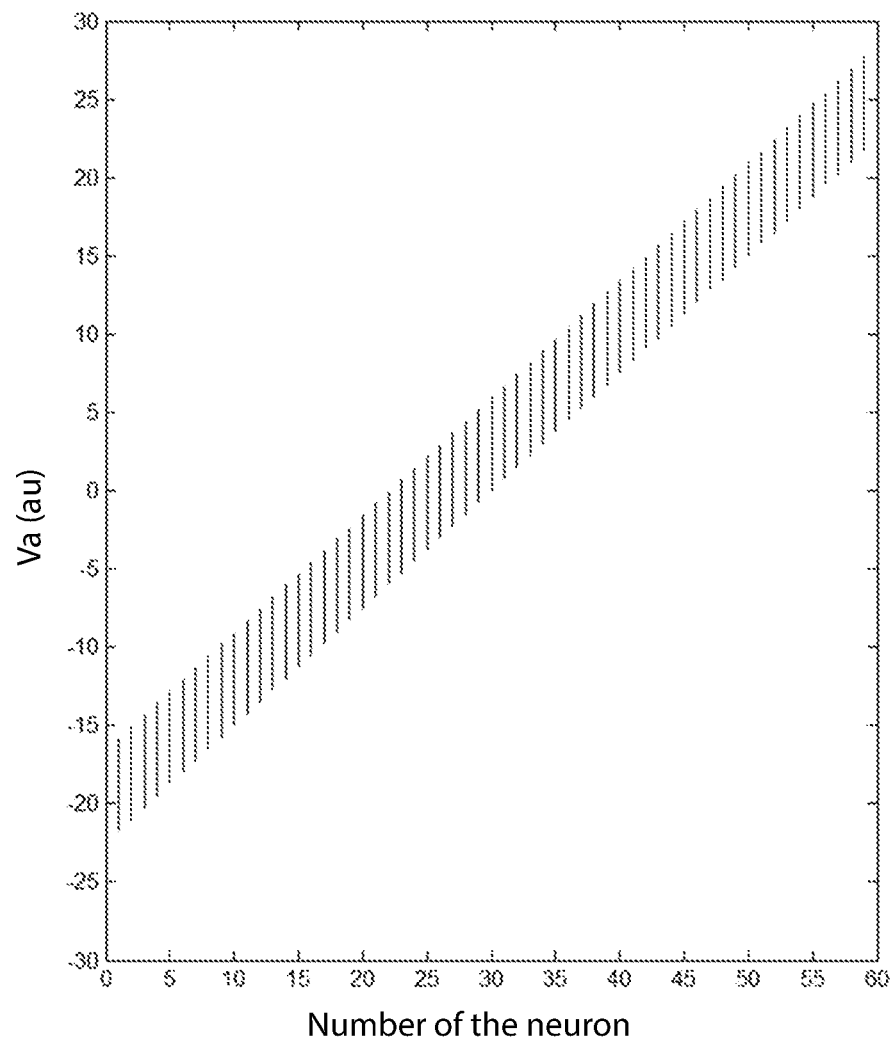
FIG. 3c schematically shows an overlap of the sensitivity intervals of the artificial neurons of the input layer of the first network of artificial neurons of FIG. 2b.

FIG. 3a schematically shows the input layer 11 when it receives the electrical signal dIn then converts the amplitude of the electrical signal dIn into a train of first spikes. FIG. 3b schematically illustrates the definition of a margin Mar around an amplitude value Va to obtain a sensitivity interval Sen of an artificial neuron of the input layer n11. FIG. 3c schematically shows an overlap of the sensitivity intervals Sen of the artificial neurons of the input layer n11. FIGS. 3a, 3b and 3c are described jointly.

The input layer 11 is typically a matrix of artificial neurons n11 comprising Na lines and Nt columns. The number Nt of columns is typically chosen as a function of a time frame for observing the electrical signal dIn, in such a way that the artificial neurons n11 of a same column receive the electrical signal at a same given instant.

The number Na of lines is typically chosen as a function of a range of values in which the amplitude of the electrical signal is variable, in such a way that:
- the artificial neurons n11 of a same line are activated for a same amplitude value of the electrical signal dIn, and the artificial neurons of distinct lines are activated for distinct amplitude values Va of the electrical signal dln.

Each artificial neuron n11 of a same column is thus associated with a distinct amplitude value Va of the electrical signal dln in such a way that all of the artificial neurons n11 of a same column scan the range of values in which the amplitude of the electrical signal dln is variable.

At each instant $t_n=n*dt$, with n a natural integer and dt a time step, a first column $C_0$ of artificial neurons n11 receives the electrical signal dln and as a function of the amplitude value of the electrical signal dln received, at least one artificial neuron n11 of the first column $C_0$ emits a spike that is transmitted to the intermediate layer 13. In FIG. 3a, an artificial neuron emitting a spike is referenced 11_1 and represented by a full circle whereas an artificial neuron not emitting a spike is referenced 11_0 and represented by an empty circle.

A margin Mar is preferentially defined around each amplitude value Va of the electrical signal dln received in such a way that each artificial neuron of the input layer n11 has a sensitivity interval Sen. Thus, an artificial neuron of the input layer n11 emits a spike when the amplitude value Va of the electrical signal dln is in the sensitivity interval of said artificial neuron n11. The number Na of lines and the size of the sensitivity intervals Sen are preferentially chosen as a function of the range of values in which the amplitude of the electrical signal is variable in such a way that:
  all of the sensitivity intervals Sen scan the range of values in which the amplitude of the electrical signal dln is variable, and
  the artificial neurons n11 of consecutive lines have their sensitivity intervals Sen that overlap.

Thanks to the sensitivity intervals Sen and their overlap, at each instant $t_n=n*dt$:
  the first column $C_0$ of artificial neurons n11 receives a sample of the electrical signal dln, and
  at least two artificial neurons n11 of the first column $C_0$ each emit a spike, each spike being transmitted to the intermediate layer 13.

In the particular example of FIG. 3c, the margin Mar around each amplitude value Va is chosen equal to 1.5 times the noise level and the width of the sensitivity interval Sen is thus equal to 3 times the noise level. This choice ensures a probability distribution of the spikes enabling good learning. The overlap of the sensitivity intervals Sen is next configured in order that eight artificial neurons n11 of the first column $C_0$ emit a spike at each instant $t_n$.

The number Nt of columns being strictly greater than 1, at each instant $t_k=t_n+k*dt'$ and for each column $C_k$ of artificial neurons n11, with dt' a second time step and k a natural integer such that $1≤k<(Nt-1)$, each artificial neuron n11 of same line as an artificial neuron n11 of the first column $C_0$ having emitted a spike at the instant tn, emits in its turn a spike that is transmitted to the intermediate layer 13. The number Nt of columns is preferably chosen such that the time frame for observing the electrical signal dln is slightly less than the minimum duration of an action potential. In an exemplary embodiment, the time frame for observing the electrical signal dln is chosen equal to 0.9 ms. In an exemplary embodiment, the second time step dt' is equal to the time step dt.

In the embodiment that has been described until now, each artificial neuron n11 of the input layer is sensitive to an amplitude value at a given instant. Alternatively, each artificial neuron n11 of the input layer may be sensitive to the amplitude values in a given time sensitivity window. In this case, an artificial neuron n11 of the input layer emits a spike if at least one of the amplitude values received during its sensitivity time window is in its sensitivity interval. This alternative embodiment may bring greater robustness to the method 100 according to one aspect of the invention, particularly when the electrical signal associated with an action potential comprises rapid amplitude variations, which has the consequence that the amplitude values sampled strongly depend on the synchronization between said action potential and the sampling.

The behavior of the artificial neurons of the intermediate layer n13 and the artificial neurons of the output layer n15 is typically defined by an LIF (Leaky-Integrate-and-Fire) model. According to this LIF model, each artificial neuron has a potential, also called membrane potential or trans-membrane potential, and each synapse has a weight, also called synaptic weight. Each time that an artificial neuron receives a spike via a synapse, the potential of this artificial neuron is modified proportionally to the weight of this synapse. In the case of an excitatory synapse, the potential of the artificial neuron is increased proportionally to the weight of this synapse; in the case of an inhibitory synapse, the potential of the artificial neuron is decreased proportionally to the weight of this synapse.

When the potential of an artificial neuron reaches a certain threshold value Th, the artificial neuron emits a spike and its potential is brought back to a reset value $V_{RESET}$. The reset value $V_{RESET}$ is notably chosen as a function of the threshold value: the objective is that the value of the potential of an artificial neuron having emitted a spike is brought back to a value close to the value of the rest potential, or less than the value of the rest potential.

According to the LIF model, the value of the potential of each artificial neuron respects the following equation:

$$\frac{dV}{dt} = -\frac{1}{\tau_m} \cdot V(t) + \sum_i \sum_s w_i(t_s)\delta(t-t_{i,s}) + \sum_f (V_{reset} - V(t_f))\delta(t-t_f)$$

$T_m$ is the characteristic membrane time of the artificial neuron considered; I indexes each incoming synapse, of weight w, of the artificial neuron considered; s indexes the spikes received by the artificial neuron considered by each synapse i, with their arrival time $t_{i,s}$; f indexes the spikes emitted by the artificial neuron considered with their emission time $t_f$.

The values of the characteristic time $T_m$ and the threshold value Th are chosen as a function of the layer considered. The choice of the threshold value depends on the number of spikes expected for the layer considered.

For each artificial neuron n13 of the intermediate layer:
  the characteristic membrane time $T_m$ is preferentially comprised in the interval [dt; 6*dt]; generally speaking, since the artificial neurons n13 of the intermediate layer learn portions, at a given instant, of waveform of action potentials, preferentially for the artificial neurons n13 of the intermediate layer a characteristic time $T_m$ of the same order of magnitude as the sampling period dt is chosen;
  the threshold value Th is chosen so as to be slightly greater than the potential of the artificial neurons when the electrical signal only contains noise;
  the reset value VRESET is preferentially comprised in the interval [−100*Th; 0].

According to a particular exemplary embodiment, for each artificial neuron n13 of the intermediate layer:
  the characteristic membrane time $T_m$ is equal to 3*dt;

the threshold value Th is equal to Nt*overlap*0.75 with Nt the number of columns of the input layer and "overlap" the overlap of the sensitivity intervals Sen of the artificial neurons of the input layer which is set at 8 in the particular example of FIG. 3c;

the reset value $V_{RESET}$ is equal to −20*Th.

For each artificial neuron n15 of the output layer:

the characteristic membrane time $T_m$ is preferentially comprised in the interval [1 ms; 4 ms]; generally speaking, since the role of each artificial neuron n15 of the output layer is to learn the whole of an action potential, the characteristic time $T_m$ of the artificial neurons n15 of the output layer is preferentially chosen of the order of the duration of an action potential;

the reset value $V_{RESET}$ is preferentially comprised in the interval [−20*Th; 0].

According to a particular exemplary embodiment, for each artificial neuron n15 of the output layer:

the characteristic membrane time $T_m$ is equal to 2.5 ms;

the reset value $V_{RESET}$ is equal to −5*Th.

It is advantageously provided that each artificial neuron of the intermediate layer, after having emitted a spike, is prevented from emitting another spike during a refractory period. This refractory period is typically of the order of magnitude of the duration of a sampling period dt and preferentially comprised in the interval [dt; 10*dt]. In the particular exemplary embodiment, the refractory period is 5*dt. Similarly, it is advantageously provided that each artificial neuron of the output layer, after having emitted a spike, is prevented from emitting another spike for a second refractory period. This second refractory period is typically of the order of magnitude of the duration of an action potential, preferentially comprised between 0.5 ms and 10 ms and more preferentially comprised between 1 ms and 4 ms. In the particular exemplary embodiment, the refractory period is 2.5 ms. The weight of each first excitatory synapse se1 is preferentially normalized: the weight of each first excitatory synapse se1 then belongs to the interval [0; 1]. The weight of each second excitatory synapse se2 is preferentially normalized: the weight of each second excitatory synapse se2 then belongs to the interval [0; 1].

Each excitatory synapse, that is to say each first excitatory synapse se1 and each second excitatory synapse se2 in the case of the network of artificial neurons 10, advantageously respects a STDP rule which modifies its weight as a function of the instants at which the presynaptic spikes and the postsynaptic spikes respectively occur. Typically, for each excitatory synapse, a coincidence time window Δt between presynaptic and postsynaptic spikes is defined:

$$\Delta t = -[-T_{stdp-}; +T_{stdp+}]$$

where $T_{stdp-}$; is a duration measured upstream of each presynaptic spike received by said excitatory synapse and $T_{stdp+}$ is a duration measured downstream of each presynaptic spike received by said excitatory synapse.

This coincidence time window is preferentially chosen as a function of the positioning of each excitatory synapse within the network of artificial neurons. For each first excitatory synapse si1:

$T_{stdp+}$ belongs preferentially to the interval [0; 3*dt] and in the particular exemplary embodiment, $T_{stdp+}$ is equal to 1*dt;

$T_{stdp-}$ belongs preferentially to the interval [0; 3*dt] and in the particular exemplary embodiment, $T_{stdp-}$ is equal to 0.

For each second excitatory synapse si2:

$T_{stdp+}$ belongs preferentially to the interval [1 ms; 3 ms] and in the particular exemplary embodiment, $T_{stdp+}$ is equal to 1.5 ms;

$T_{stdp-}$ belongs preferentially to the interval [1 ms; 3 ms] and in the particular exemplary embodiment, $T_{stdp-}$ is equal to 1.5 ms.

Figure 4A:
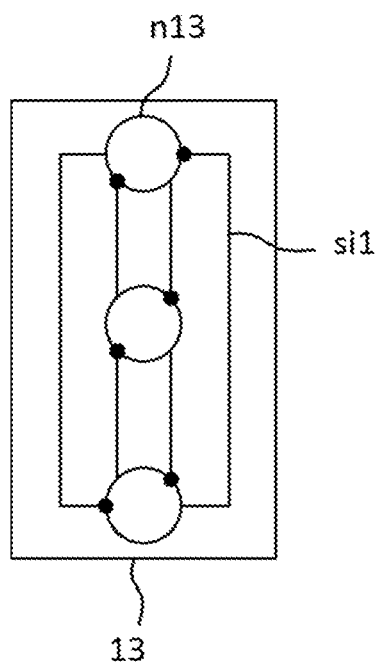
FIG. 4a schematically shows a plurality of first inhibitory synapses interconnecting the artificial neurons of the intermediate layer of the first network of artificial neurons of FIG. 2b.
Figure 4B:
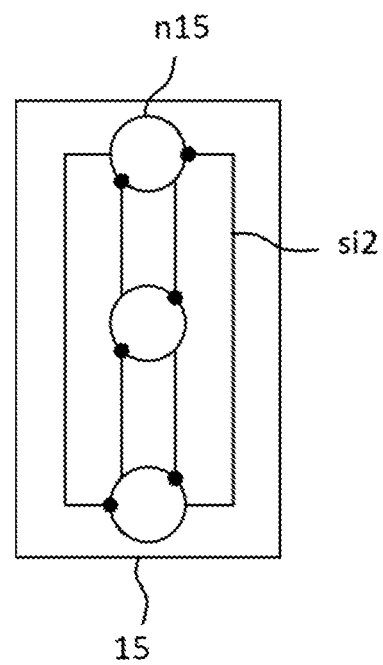
FIG. 4b schematically shows a plurality of second inhibitory synapses interconnecting the artificial neurons of the output layer of the first network of artificial neurons of FIG. 2b.

Advantageously a "winner takes all" type mechanism is used within the intermediate layer 13 and within the output layer 15. This mechanism is illustrated in FIGS. 4a and 4b, which are described jointly. According to this mechanism, each artificial neuron n13 of the intermediate layer is connected to all the other artificial neurons n13 of the intermediate layer by a plurality of first inhibitory synapses sit. Similarly, each artificial neuron n15 of the output layer is connected to all the other artificial neurons n15 of the output layer by a plurality of second inhibitory synapses si2. Thus, an artificial neuron emitting a spike at a given instant laterally inhibits the other neurons of the same layer in order to prevent them from emitting, also, a spike at the same instant.

This lateral inhibition contributes such that the artificial neurons of the intermediate and output layers learn to emit spikes for different input waveforms. It is in fact possible that several artificial neurons of a same layer have a tendency to learn the same waveforms. In this case, the lateral inhibition constrains these artificial neurons not to emit their spikes exactly at the same moment, thus to shift their emissions while respecting a certain latency delay. The latency delay is determined by the configuration of the lateral inhibition: the higher the lateral inhibition, the greater the latency delay. Thus, thanks to the lateral inhibition, the artificial neurons of a same layer learn either to emit spikes for different input action potentials, or to emit spikes for different parts of a same input action potential. The weight of each first inhibitory synapse si1 is preferentially comprised in the interval [0.1*Th; 0.5*Th], with Th the threshold value of each artificial neuron n13 of the intermediate layer. In the particular exemplary embodiment, the weight of each first inhibitory synapse si1 is equal to 0.2*Th.

The weight of each second inhibitory synapse si2 is preferentially comprised in the interval [1*Th; 10*Th], with Th the threshold value of each artificial neuron n15 of the output layer. In the particular exemplary embodiment, the weight of each second inhibitory synapse si2 is equal to 10*Th.

An STDP (spike-timing-dependent plasticity) rule may also be implemented for each inhibitory synapse, that is to say for each first inhibitory synapse si1 and for each second inhibitory synapse si2 in the case of the network of artificial neurons 10, according to which;

the weight of each inhibitory synapse increases in the event of coincidence of a postsynaptic spike and a presynaptic spike in a certain time window, and the weight of each inhibitory synapse decreases in the case of a presynaptic spike only in the time window considered.

In the case of a postsynaptic spike only in the time window considered, the weight of each inhibitory synapse may remain unchanged. Alternatively, the weight of each inhibitory synapse may decrease in the event of a postsynaptic spike only in the time window considered.

In addition to the mechanism of lateral inhibition of "winner take all" type that has been described, each second excitatory synapse se2 advantageously respects a STDP rule that modifies its weight as a function of the instants at which take place respectively the presynaptic spikes and the lateral inhibitions. Alternatively, said STDP rule may be implemented both for the first excitatory synapses se1 and for the second excitatory synapses se2, or only for the first excitatory synapses se1. Typically, for each excitatory synapse, a coincidence time window between excitation and inhibition is defined, as described previously.

According to an embodiment, the STDP rule implemented for each excitatory synapse is the following:
- the weight of an excitatory synapse remains unchanged when its predefined time window comprises a presynaptic spike only;
- the weight of an excitatory synapse is decreased, for example by a quantity $a_{post}$, when its predefined time window comprises a postsynaptic spike only;
- the weight of an excitatory synapse is increased, for example by a quantity $(a_{pair}-a_{post})$, when its predefined time window comprises a presynaptic spike and a postsynaptic spike.

According to this embodiment, the weight of each excitatory synapse remains comprised between 0 and a maximum value that is typically 1 for normalized weight.

Alternatively, the weight of an excitatory synapse may only be increased when its predefined time window comprises a postsynaptic spike succeeding a presynaptic spike. According to this alternative, when the predefined time window comprises a presynaptic spike succeeding a postsynaptic spike, the weight of the excitatory synapse considered remains unchanged or is decreased.

For each artificial neuron n13 of the intermediate layer, the quantity $a_{pair}$ is preferentially comprised in the interval [0.001; 0.01] and the quantity $a_{post}$ is preferentially comprised in the interval [$0.4*a_{pair}$; $0.8*a_{pair}$]. In the particular exemplary embodiment, for each artificial neuron n13 of the intermediate layer, the quantity $a_{pair}$ is 0.003 and the quantity $a_{post}$ is $0.65*a_{pair}$.

For each artificial neuron n15 of the output layer, the quantity $a_{pair}$ is preferentially comprised in the interval [0.001; 0.02] and the quantity $a_{post}$ is preferentially comprised in the interval [$0.4*a_{pair}$; $0.7*a_{pair}$]. In the particular exemplary embodiment, for each artificial neuron n15 of the output layer, the quantity $a_{pair}$ is 0.01 and the quantity $a_{post}$ is $0.5*a_{pair}$.

According to another embodiment, the STDP rule implemented for each excitatory synapse is the following:
- when an artificial neuron of the intermediate layer n13 or the output layer n15 receives, in the predefined coincidence time window between excitation and inhibition, a spike transmitted by an excitatory synapse and a lateral inhibition transmitted by another artificial neuron of the same layer, the weight of said excitatory synapse is decreased by a quantity $(a_{lat}-a_{pre})$;
- when an artificial neuron of the intermediate layer n13 or the output layer n15 receives, in the predefined coincidence time window between excitation and inhibition, a spike transmitted by an excitatory synapse and no lateral inhibition transmitted by another artificial neuron, the weight of said excitatory synapse is increased by a quantity $a_{pre}$.

For each artificial neuron n15 of the output layer, the quantity $a_{lat}$ is preferentially comprised in the interval [0; $0.2*a_{pair}$] and the quantity $a_{pre}$ is preferentially comprised in the interval [0; $0.5*a_{lat}$]. In the particular exemplary embodiment, for each artificial neuron n15 of the output layer, the quantity $a_{lat}$ is $0.1*a_{pair}$ and the quantity $a_{pre}$ is $0.01*a_{pair}$.

According to another embodiment, the two STDP rules that have been described may be implemented simultaneously. In this case, each excitatory synapse has a first predefined time window for the implementation of the first STDP rule and a second predefined time window for the implementation of the second STDP rule, and the first and second predefined time windows for each excitatory synapse may be identical or distinct.

The number of artificial neurons n13 of the intermediate layer is chosen sufficiently large so that all possible patterns can be learnt. The number of artificial neurons n13 of the intermediate layer thus depends on the number of different types of action potentials to detect and the latency delay configured for the intermediate layer 13. A too high number of artificial neurons n13 does not modify the operation of the network of artificial neurons but has a drawback in terms of computing time. A too low number of artificial neurons n13 limits the possibilities of learning patterns. In practice, the number of artificial neurons n13 of the intermediate layer is preferentially comprised in the interval [30; 200]. In the particular exemplary embodiment, the intermediate layer comprises 80 artificial neurons n13.

The number of artificial neurons n15 of the output layer is chosen greater than or equal to the number of different types of action potentials to detect. In practice, since the number of action potentials to detect is not generally known in advance, the number of artificial neurons n15 of the output layer is preferentially comprised in the interval [3; 30] and more preferentially comprised in the interval [7; 15], In the particular exemplary embodiment, the output layer comprises 10 artificial neurons n15.

The artificial neurons n13 of the intermediate layer advantageously respect a STP (short term plasticity) rule which will now be described. The role of the artificial neurons n11 of the input layer is to convert the electrical signal dIn into a form that is exploitable by the artificial neurons n13 of the intermediate layer. The artificial neurons n11 of the input layer thus convert the electrical signal dIn into a train of first spikes. The role of the artificial neurons n13 of the intermediate layer is next to learn to recognize waveforms or parts of waveforms. To do so, it is wished that the artificial neurons n13 of the intermediate layer manage to filter noise in order that they learn to recognize noise. The short term plasticity rule STP contributes to this objective.

Each first excitatory synapse se1, which connects an artificial neuron n11 of the input layer, designated presynaptic artificial neuron, to an artificial neuron n13 of the intermediate layer, designated postsynaptic artificial neuron, is considered. According to the STP rule, the weight of each first excitatory synapse se1 is allotted a synaptic coefficient $P_{rel}$ such that $0 \leq P_{rel} \leq 1$.

Each postsynaptic artificial neuron n13 receiving a spike via a first excitatory synapse se1 is excited proportionally to the product of the synaptic coefficient $P_{rel}$ and the weight of said first excitatory synapse. The synaptic coefficient $P_{rel}$ decreases when the presynaptic artificial neuron n11 emits a spike, and the synaptic coefficient $P_{rel}$ increases towards 1 otherwise. According to one embodiment, the synaptic coefficient respects the following equation:

$$\frac{dP_{rel}}{dt} = \frac{1}{\tau_{stp}}(1-P_{rel}) - \sum_s P_{rel} \cdot f_d \delta(t-t_s)$$

Where s indexes the presynaptic spikes, that is to say the spikes emitted by the presynaptic artificial neurons n11, each presynaptic spike taking place at an instant $t_s$. Each time that a postsynaptic artificial neuron n13 receives a spike via a first excitatory synapse se1, the synaptic coefficient $P_{rel}$ of said first excitatory synapse se1 is decreased by the quantity $P_{rel}*f_d$, where $f_d$ is the degree of depression. The degree of depression $f_d$ is chosen such that an artificial neuron n11 of the input layer that discharges at each time step has a low synaptic coefficient $P_{rel}$. When the first excitatory synapse se1 does not transmit any spike, its synaptic coefficient $P_{rel}$ tends towards 1 in a characteristic time $T_{stp}$. The characteristic time $T_{stp}$ is preferentially comprised between 0.1 ms and 10 ms and more preferentially comprised between 0.5 ms and 3 ms. The characteristic time $T_{stp}$ is typically of the order of magnitude of the duration of an action potential. In the particular exemplary embodiment, the characteristic time $T_{stp}$ is equal to 1.5 ms. In the particular exemplary embodiment, the degree of depression $f_d$ is chosen such that:

$$f_d = 1 - \exp\left(-6.5 * \frac{dt}{\tau_{stp}}\right)$$

The short term plasticity rule STP uses the fact that the artificial neurons n11 of the input layer associated with the noise amplitude values have a tendency to emit spikes permanently: thanks to the short term plasticity rule STP, the more an artificial neuron n11 of the input layer emits spikes, the more the excitation capacity of each first excitatory synapse se1 connecting this artificial neuron n11 of the input layer to the artificial neurons n13 of the intermediate layer decreases. According to the LIF model that is used to define the behavior of the artificial neurons n13 of the intermediate layer, the potential of each artificial neuron n13 then increases during the reception of spikes via excitatory synapses, and tends towards a rest value otherwise. When the electrical signal dIn only contains noise, which is converted by the input layer 11 into a train of first spikes, constant, and relatively low because $P_{rel}$ is low, and the potential of the artificial neurons n13 of the intermediate layer stabilizes around a value greater than the rest value. The threshold of the artificial neurons n13 of the intermediate layer is chosen greater than this stabilization value, in order that the artificial neurons n13 of the intermediate layer do not emit a spike when they receive noise. At the same time, the threshold of the artificial neurons n13 of the intermediate layer is chosen in such a way that the increase in potential linked to the arrival of an action potential, and thus to the emission by the input layer of a series of spikes with a greater excitation capacity because $P_{rel}$ is large, leads to the emission of at least one spike.

The different action potentials to detect and to sort generally have different durations and different amplitudes. Consequently, two distinct action potentials typically lead to the activation of different groups of artificial neurons n11 of the input layer and the transmission to the artificial neurons n13 of the intermediate layer then to the artificial neurons n15 of the output layer of trains of spikes of different sizes, that is to say not comprising the same number of spikes. The spike emission threshold of the artificial neurons n15 of the output layer must be configured sufficiently low so that waveforms of short duration, for which the number of spikes emitted by the artificial neurons of the intermediate layer n13 is low, can be detected. However, if the spike emission threshold of the artificial neurons n15 of the output layer is defined at a low value making it possible to detect waveforms of short duration, the artificial neurons n15 of the output layer which learn to recognize waveforms of long duration corresponding to trains of spikes of large size are going to emit spikes before the trains of spikes have finished being transmitted to them by the artificial neurons n13 of the intermediate layer. In this case, since each long train of spikes is going to stop being transmitted after an artificial neuron n15 of the output layer has emitted a spike, another artificial neuron n15 of the output layer is going to be able to learn to recognize the end of the waveform corresponding to the long train of spikes. In order to prevent this undesirable behavior, it is possible to define a high lateral inhibition.

Nevertheless, a too high lateral inhibition is not desirable because different action potentials may take place one after the other in a short time interval: in such a case, it is wished that the artificial neurons n15 of the output layer are capable of emitting spikes one after the other in a sufficiently short time interval. In addition, even if a sufficiently high lateral inhibition is defined to guarantee that a single artificial neuron n15 of the output layer does not emit a spike for a given waveform, only the start of the long trains of spikes will be taken into account, which will prevent differentiating two waveforms before an identical start and a different end.

It is desired that the sorting method according to one aspect of the invention is robust to such variations of amplitude and duration of action potentials, in order that the output layer 15 still only emits a single spike for each occurrence of each type of action potential detected while being capable of detecting all the types of action potential, independently of their length.

To do so, a plasticity rule is advantageously introduced on the spike emission threshold Th of each artificial neuron n15 of the output layer, in order that the spike emission threshold of each artificial neuron n15 of the output layer adapts to the waveform that it is in the course of learning, and thus the size of the train of spikes corresponding to the waveform that it is in the course of learning. When a plasticity rule is implemented on the threshold Th of each artificial neuron n15 of the output layer 15, the initial threshold Th is preferentially chosen very low, that is to say for example equal to 1. The threshold Th is then adjusted as a function of its plasticity rule. In the absence of implementation of such a plasticity rule, the threshold Th of each artificial neuron n15 of the output layer 15 is preferentially chosen in the interval [3; 10]. Two possible implementations of the plasticity rule on the threshold Th of each artificial neuron of the output layer will now be described.

According to a first alternative embodiment, a time window is defined around each postsynaptic spike emitted by an artificial neuron n15 of the output layer and the plasticity rule on the spike emission threshold of each artificial neuron n15 of the output layer is the following:

the threshold value of each artificial neuron n15 of the output layer emitting a spike at an instant t is increased proportionally to the number of spikes Ni received by said artificial neuron n15 in the time window defined:

$$Th(t) = Ni * \Delta_{Th+};$$

the threshold value of each artificial neuron n15 of the output layer emitting a spike at an instant t1 is decreased in such a way that:

$$Th(t2) = \alpha * Th(t1)$$

with Th(t1) the threshold value at the instant t1, Th(t2) the threshold value at an instant t2 later than the instant t1 and $\alpha$ a real number such that $0 < \alpha < 1$.

$\alpha$ belongs preferentially to the interval [0.95; 0.999]; in the particular exemplary embodiment, $\alpha$ is equal to 0.99. The time window around the instant t may be comprised between 0.1 ms and 20 ms, preferentially between 1 and 3 ms, and is typically 2 ms around the instant t.

$\alpha_{Th+}$ belongs preferentially to the interval [0.5*(1−α); 0.8*(1−α)]. In the particular exemplary embodiment, $\Delta_{Th+}$ is equal to 0.6*(1−α).

Consequently, when a given action potential takes place, the artificial neuron n15 of the output layer learning to recognize this action potential receives a train of N presynaptic spikes, which leads to an increase in its spike emission threshold proportional to N, and emits a postsynaptic spike, which leads to a reduction in its spike emission threshold proportional to the value of the spike emission threshold. The spike emission threshold thus tends towards a value that is proportional to the average number of presynaptic spikes. It is desired that a majority of presynaptic spikes is taken into account before emitting a postsynaptic spike. It may however happen that certain presynaptic spikes, normally present, are missing. In order to be able to emit a postsynaptic spike even if only a part of the presynaptic spikes expected is present, the spike emission threshold thus must not be too high. It thus involves finding a compromise between taking into account the majority of presynaptic spikes and being robust to potential errors of the intermediate layer 13. In practice, a spike emission threshold is preferentially chosen equal to between 0.3 and 0.8 times the average number of presynaptic spikes emitted during the occurrence of an action potential.

According to a second alternative embodiment, a first time window is defined before each postsynaptic spike and a second time window after each postsynaptic spike, and the plasticity rule on the spike emission threshold of each artificial neuron n15 of the output layer is the following;
    when an artificial neuron n15 of the output layer receives a presynaptic spike in the first predefined time window, the spike emission threshold of said artificial neuron n15 of the output layer is decreased;
    when an artificial neuron n15 of the output layer receives a presynaptic spike in the second predefined time window, the spike emission threshold of said artificial neuron n15 of the output layer is increased.

The first time window before each postsynaptic spike may be comprised between 0.1 ms and 20 ms, preferentially between 1 and 3 ms, and is typically 2 ms. The second time window after each postsynaptic spike may be comprised between 0.1 ms and 20 ms, preferentially between 1 and 3 ms, and is typically 2 ms.

Consequently, the spike emission threshold of each artificial neuron n15 of the output layer adapts in such a way that each artificial neuron n15 of the output layer emits a postsynaptic spike after having received a number of presynaptic spikes proportional to the total number of presynaptic spikes received for the duration of the corresponding waveform. As previously, it involves finding a compromise between taking into account the majority of presynaptic spikes and being robust to potential errors of the intermediate layer 13. In practice, a spike emission threshold equal to between 0.3 and 0.8 times the totality of the presynaptic spikes emitted during the occurrence of an action potential is preferentially chosen.

Figure 5:
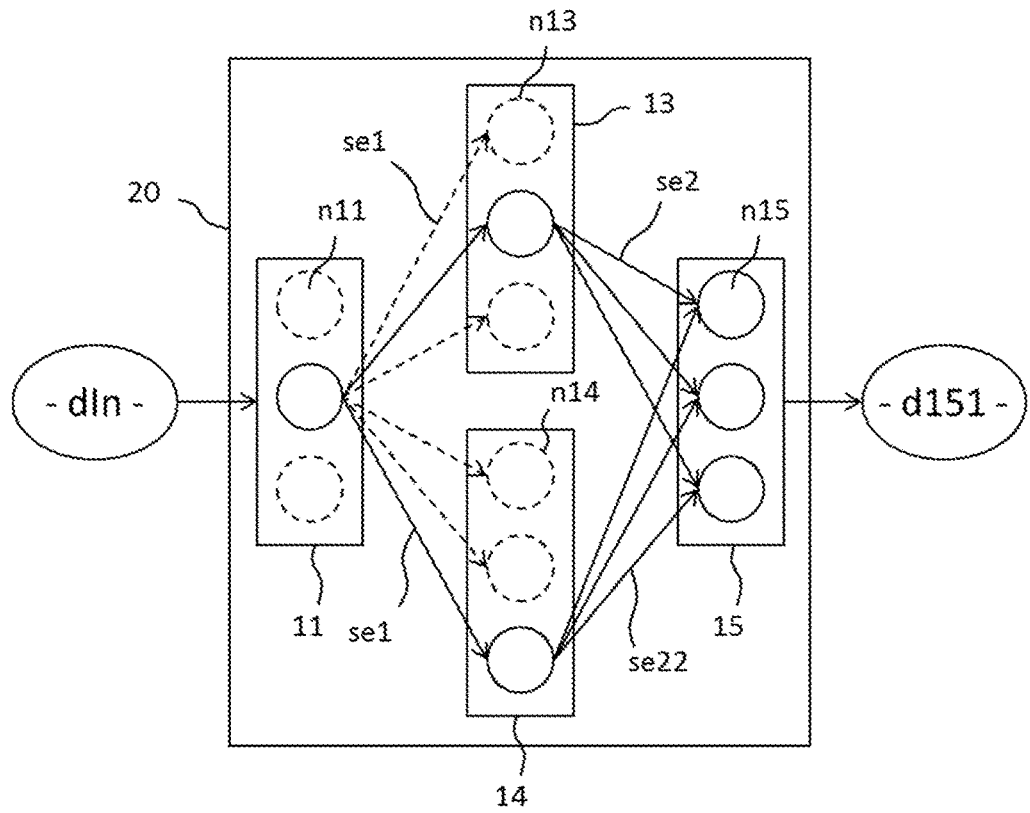

In relation with FIGS. 5 to 8, several alternative embodiments of networks of artificial neurons will now be described for the implementation of the method 100 for unsupervised sorting, in real time, of action potentials of a plurality of biological neurons according to one aspect of the invention. FIG. 5 schematically shows a second network of artificial neurons 20 for the implementation of the method 100 according to one aspect of the invention, comprising two intermediate layers in parallel. The second network of artificial neurons 20 comprises:
    the input layer 11 comprising the plurality of artificial neurons n11,
    the intermediate layer 13 comprising the plurality of artificial neurons n13,
    a second intermediate layer 14 comprising a plurality of artificial neurons n14, and
    the output layer 15 comprising the plurality of artificial neurons n15.

The plurality of first excitatory synapses se1 connects each artificial neuron of the input layer n11 to the plurality of artificial neurons of the intermediate layer n13 and to the plurality of artificial neurons of the second intermediate layer n14. The plurality of second excitatory synapses se2 connects each artificial neuron of the intermediate layer n13 to the plurality of artificial neurons of the output layer n15. A second plurality of second excitatory synapses se22 connects each artificial neuron of the second intermediate layer n14 to the plurality of artificial neurons of the output layer n15.

The input layer 11 transmits the train of first spikes to the intermediate layer 13 and to the second intermediate layer 14 via the plurality of first excitatory synapses se1. The intermediate layer 13 converts the train of first spikes into a train of second spikes and transmits the train of second spikes to the output layer 15 via the plurality of second excitatory synapses se2. The second intermediate layer 14 converts the train of first spikes into a second train of second spikes and transmits the second train of second spikes to the output layer 15 via the second plurality of second excitatory synapses se22. The output layer then uses the train of second spikes and the second train of second spikes to sort each occurrence of each type of action potential present in the electrical signal dln.

Figure 6:
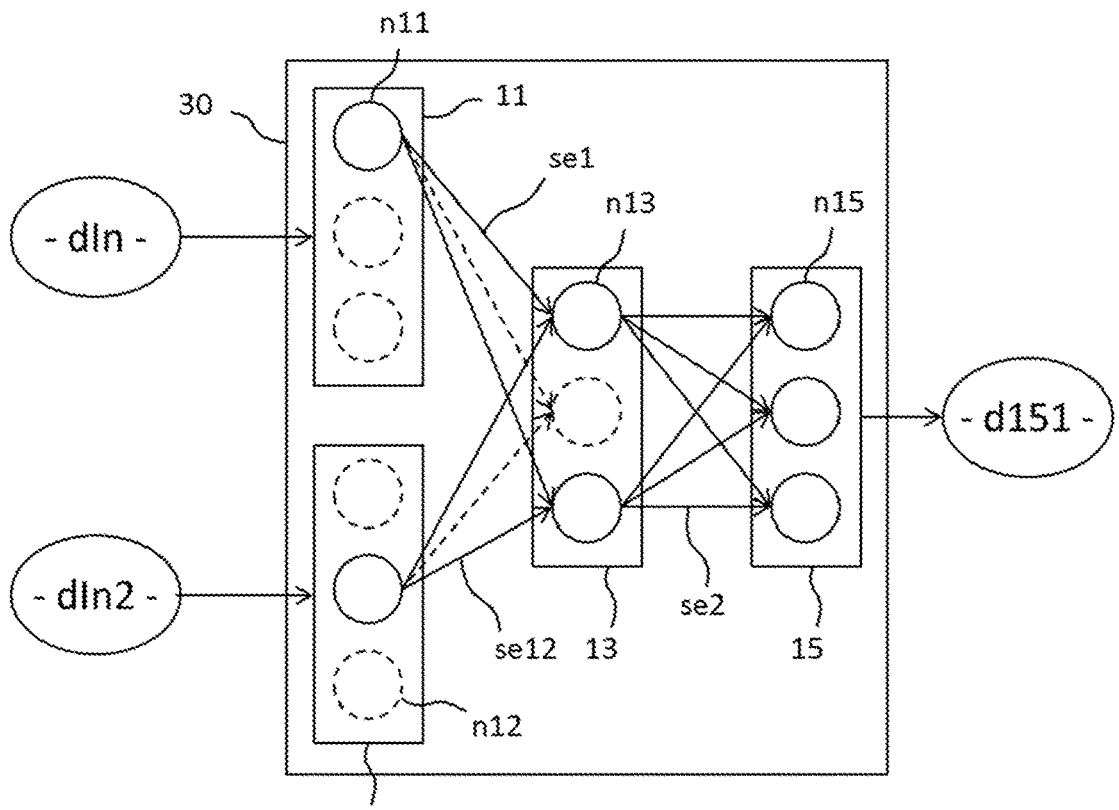

FIG. 6 schematically shows a third network of artificial neurons 30 for the implementation of the method 100 according to one aspect of the invention, comprising two input layers in parallel. The third network of artificial neurons comprises:
    the input layer 11 comprising the plurality of artificial neurons n11,
    a second input layer 12 comprising a plurality of artificial neurons n12,
    the intermediate layer 13 comprising the plurality of artificial neurons n13 and
    the output layer 15 comprising the plurality of artificial neurons n15.

The plurality of first excitatory synapses se1 connects each artificial neuron of the input layer n11 to the plurality of artificial neurons of the intermediate layer n13. A second plurality of first excitatory synapses se12 connects each artificial neuron of the second input layer n12 to the plurality of artificial neurons of the intermediate layer n13.

The plurality of second excitatory synapses se2 connects each artificial neuron of the intermediate layer n13 to the plurality of artificial neurons of the output layer n15.

The input layer 11 receives the electrical signal din and the second input layer 30 receives a second electrical signal dln2. The second electrical signal dln2 measures an electrical activity of a second plurality of biological neurons and has a variable amplitude as a function of action potentials emitted by the plurality of second biological neurons over time. The second electrical signal dln2 may be different from the electrical signal dln or identical to the electrical signal dln. The second plurality of biological neurons of which the electrical activity is measured by the second electrical signal dln2 may be partially or totally different from the plurality of biological neurons of which the electrical activity is measured by the electrical signal dIn. Alternatively, the second plurality of biological neurons of which the electrical activity is measured by the second electrical signal dIn2 may be identical to the plurality of biological neurons of which the electrical activity is measured by the electrical signal dIn. The input layer 11 converts the amplitude of the first electrical signal dIn into a train of first spikes and transmits the train of first spikes to the intermediate layer 13 via the plurality of first excitatory synapses se1. The second input layer 12 converts the amplitude of the second electrical signal dIn2 into a second train of first spikes 15 and transmits the second train of first spikes to the intermediate layer 13 via the second plurality of first excitatory synapses se2. The intermediate layer 13 converts the train of first spikes and the second train of first spikes into a train of second spikes and transmits the train of second spikes to the output layer 15 via the plurality of second excitatory synapses se2. The output layer 15 then uses the train of second spikes to sort each occurrence of each type of action potential present in the electrical signal dIn and in the second electrical signal dIn2.

Figure 7:
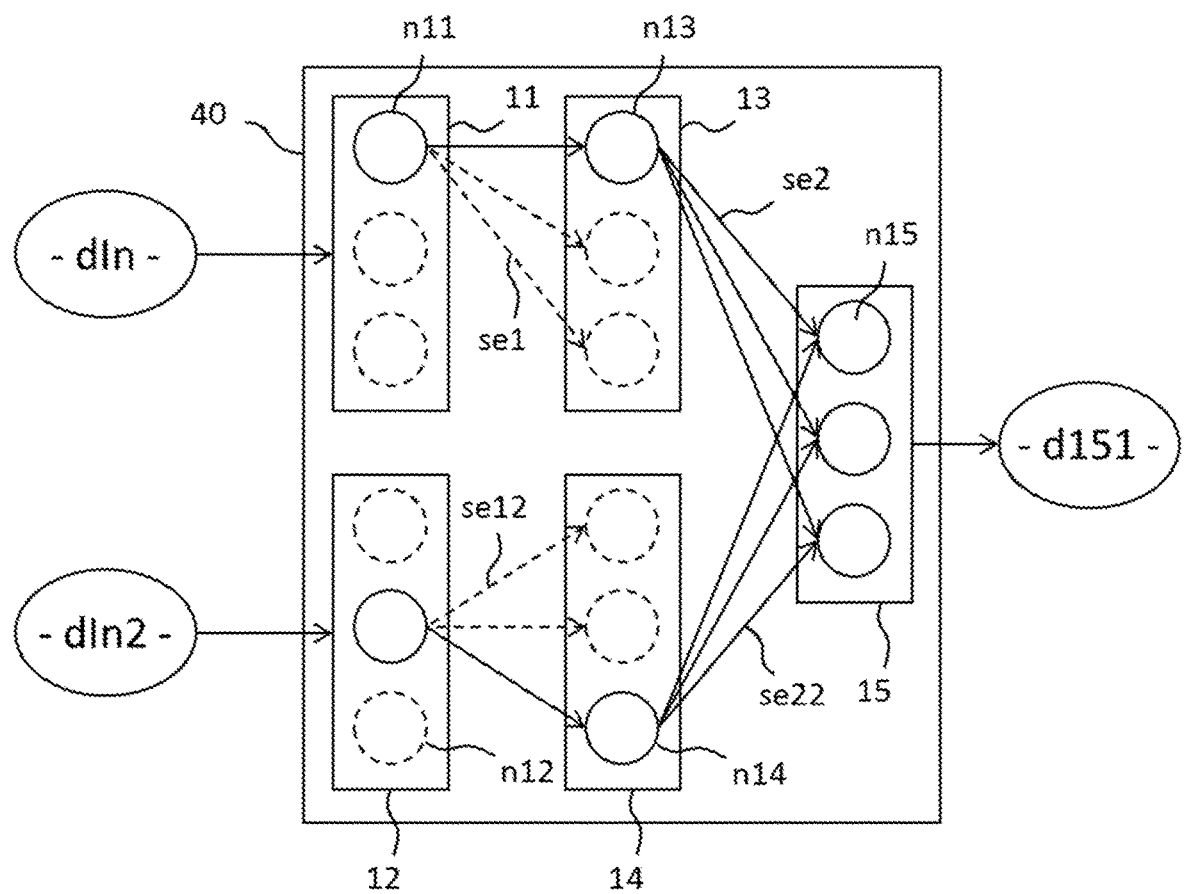

FIG. 7 schematically shows a fourth network of artificial neurons 40 for the implementation of the method 100 according to one aspect of the invention, comprising two input layers in parallel, each input layer being associated with its own intermediate layer. The fourth network of artificial neurons 40 comprises:
 the input layer 11 comprising the plurality of artificial neurons n11,
 the second input layer 12 comprising the plurality of artificial neurons n12,
 the intermediate layer 13 comprising the plurality of artificial neurons n13,
 the second intermediate layer 14 comprising the plurality of artificial neurons n14, and
 the output layer 15 comprising the plurality of artificial neurons n15.

The plurality of first excitatory synapses se1 connects each artificial neuron of the input layer n11 to the plurality of artificial neurons of the intermediate layer n13. A second plurality of first excitatory synapses se12 connects each artificial neuron of the second input layer n12 to the plurality of artificial neurons of the second intermediate layer n14. The plurality of second excitatory synapses se2 connects each artificial neuron of the intermediate layer n13 to the plurality of artificial neurons of the output layer n15. A second plurality of second excitatory synapses se22 connects each artificial neuron of the second intermediate layer n14 to the plurality of artificial neurons of the output layer n15.

The input layer 11 receives the electrical signal dIn and the second input layer receives the second electrical signal dIn2. The electrical signal dIn and the second electrical signal dIn2 have been described previously. The input layer 11 converts the amplitude of the first electrical signal dIn into a train of first spikes and transmits the train of first spikes to the intermediate layer 13 via the plurality of first excitatory synapses se1. The second input layer 12 converts the amplitude of the second electrical signal dIn2 into a second train of first spikes and transmits the second train of first spikes to the second intermediate layer 14 via the second plurality of first excitatory synapses se12. The intermediate layer 13 converts the train of first spikes into a train of second spikes and transmits the train of second spikes to the output layer 15 via the plurality of second excitatory synapses se2. The second intermediate layer 14 converts the second train of first spikes into a second train of second spikes and transmits the second train of second spikes to the output layer 15 via the second plurality of second excitatory synapses se22. The output layer 15 then uses the train of second spikes and the second train of second spikes to sort each occurrence of each type of action potential present in the electrical signal dIn and in the second electrical signal dIn2.

Figure 8:
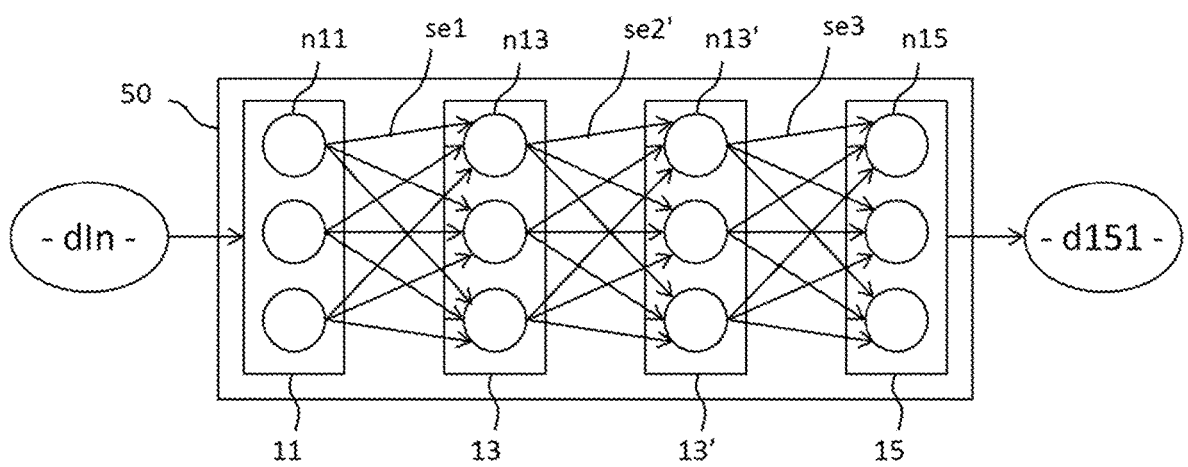

FIG. 8 schematically shows a fifth network of artificial neurons 50 for the implementation of the method 100 according to the method of the invention, comprising two intermediate layers in series. The fifth network of artificial neurons 50 comprises:
 the input layer 11 comprising the plurality of artificial neurons n11,
 the intermediate layer 13 comprising the plurality of artificial neurons n13,
 a second intermediate layer 13' comprising a plurality of artificial neurons n13',
 the output layer 15 comprising the plurality of artificial neurons n15.

The plurality of first excitatory synapses se1 connects each artificial neuron of the input layer n11 to the plurality of artificial neurons of the intermediate layer n13. A plurality of second excitatory synapses se2' connects each artificial neuron of the intermediate layer n13 to the plurality of artificial neurons of the second intermediate layer n13'. A plurality of third excitatory synapses se3 connects each artificial neuron of the second intermediate layer n13' to the plurality of artificial neurons of the output layer n15.

The input layer 11 converts the amplitude of the first electrical signal dIn into a train of first spikes and transmits the train of first spikes to the intermediate layer 13 via the plurality of first excitatory synapses se1. The intermediate layer 13 converts the train of first spikes into a train of second spikes and transmits the train of second spikes to the second intermediate layer 13' via the plurality of second excitatory synapses se2'.

The second intermediate layer 13' converts the train of second spikes into a train of third spikes and transmits the train of third spikes to the output layer 15 via the plurality of third excitatory synapses se3. The output layer 15 then uses the train of third spikes to sort each occurrence of each type of action potential present in the electrical signal dIn.

The invention claimed is:
1. A method for unsupervised sorting, in real time, of action potentials of a plurality of biological neurons by a network of artificial neurons implemented on a neuromorphic circuit, the network of artificial neurons comprising an input layer, an intermediate layer and an output layer, each artificial neuron of the input layer being connected to a plurality of artificial neurons of the intermediate layer by a plurality of first excitatory synapses and each artificial neuron of the intermediate layer being connected to a plurality of artificial neurons of the output layer by a plurality of second excitatory synapses, at least one first or second excitatory synapse connecting a first artificial neuron to a second artificial neuron and having a weight that is modified as a function of the instants at which take place presynaptic spikes emitted by the first artificial neuron and postsynaptic spikes emitted by the second artificial neuron, the method comprising:
 receiving by the input layer an electrical signal measuring an electrical activity of a plurality of biological neurons, the electrical signal having a variable amplitude as a function of action potentials emitted by the plurality of biological neurons over time, the electrical signal measuring the electrical activity of the plurality of biological neurons being directly received by the input layer such that the electrical signal is fed to the input layer without being previously encoded or stored outside of said neuromorphic circuit, or both;

converting by the input layer the amplitude of the electrical signal into a train of first spikes;

transmitting by the input layer the train of first spikes to the intermediate layer;

converting by the intermediate layer the train of first spikes into a train of second spikes;

transmitting by the intermediate layer the train of second spikes to the output layer;

as a function of the train of second spikes, sorting by the output layer each occurrence of each type of action potential present in the electrical signal.

2. The method according to claim 1, wherein, as a function of the train of second spikes, the output layer sorts each occurrence of each type of action potential present in the electrical signal by activating at the most a single group of artificial neurons of the output layer for each occurrence of an action potential in the electrical signal, each group of artificial neurons of the output layer comprising at least one artificial neuron of the output layer and being associated with a single type of action potential and each type of action potential being associated with a single group of artificial neurons of the output layer.

3. The method according to claim 2, wherein the input layer is a matrix of artificial neurons having:

Na lines, the number Na of lines being chosen as a function of a range of values in which the amplitude of the electrical signal is variable, in such a way that the artificial neurons of a same line are activated for a same amplitude value of the electrical signal, and Nt columns, the number Nt of columns being chosen as a function of a time frame for observing the electrical signal, in such a way that the artificial neurons of a same column receive the electrical signal at a same given instant;

wherein, at each instant $t_n=n*dt$, with n a natural integer and dt a time step:

a first column $C_0$ of artificial neurons receives the electrical signal, and as a function of the amplitude value of the electrical signal received, at least one artificial neuron of the first column $C_0$ emits a spike that is transmitted to the intermediate layer.

4. The method according to claim 3, wherein a margin is defined around each amplitude value of the electrical signal received in such a way that, at each instant $t_n=n*dt$:

the first column Co of artificial neurons receives the electrical signal, and as a function of the amplitude value of the electrical signal received and of the margin defined around said amplitude value, at least two artificial neurons of the first column $C_0$ each emit a spike, each spike being transmitted to the intermediate layer.

5. The method according to claim 3, wherein the number of columns Nt is strictly greater than 1 and wherein, at each instant $t_k=t_n+k*dt'$, with dt' a second time step, and for each column $C_k$ of artificial neurons, with k a natural integer such that $1 \leq k \leq Nt-1$, each artificial neuron of same line as an artificial neuron of the first column $C_0$ having emitted a spike at the instant $t_n$, emits in its turn a spike that is transmitted to the intermediate layer.

6. The method according to claim 1, wherein:

each artificial neuron of the input layer is connected to a plurality of artificial neurons of the intermediate layer by the plurality of first excitatory synapses in such a way that a spike emitted by said artificial neuron of the input layer is transmitted to the plurality of artificial neurons of the intermediate layer by the plurality of first excitatory synapses;

each artificial neuron of the intermediate layer is connected to a plurality of artificial neurons of the output layer by the plurality of second excitatory synapses in such a way that a spike emitted by said artificial neuron of the intermediate layer is transmitted to the plurality of artificial neurons of the output layer by the plurality of second excitatory synapses;

each artificial neuron of the intermediate layer and each artificial neuron of the output layer have a potential having initially a value designated "rest value"; when an excitatory synapse transmits a spike to an artificial neuron of the intermediate layer or of the output layer, the potential of said artificial neuron increases proportionally to the weight of said first excitatory synapse; when the potential of an artificial neuron of the intermediate layer or of the output layer exceeds a threshold value, said artificial neuron emits a spike and its potential is reduced to a reset value;

in the absence of spike at the input of an artificial neuron of the intermediate layer or of the output layer and when said neuron does not emit a spike itself, the potential of said neuron returns to its rest value in a characteristic time $\tau_m$.

7. The method according to claim 6, wherein the weight of each excitatory synapse is modified as a function of a predefined time window:

for a given excitatory synapse, when the predefined time window comprises a presynaptic spike and a postsynaptic spike, the weight of this excitatory synapse is increased;

for a given excitatory synapse, when the predefined time window comprises a postsynaptic spike only, the weight of this excitatory synapse is decreased;

for a given excitatory synapse, when the predefined time window comprises a presynaptic spike only, the weight of this excitatory synapse remains unchanged.

8. The method according to claim 1, wherein :

the network of artificial neurons also comprises at least one artificial detection neuron, each artificial neuron of the input layer being connected to the artificial detection neuron by a first excitatory detection synapse and the artificial detection neuron being connected to a plurality of artificial neurons of the intermediate layer by a plurality of second excitatory detection synapses;

each first excitatory detection synapse has a weight allotted a synaptic coefficient $P_{rel}$ such that $0 \leq P_{rel} \leq 1$, the synaptic coefficient $P_{rel}$ decreasing when the presynaptic artificial neuron emits a spike, and the synaptic coefficient $P_{rel}$ increasing towards 1 otherwise with a characteristic time $\tau_{stp}$;

the artificial detection neuron receiving a spike via a first excitatory detection synapse is excited proportionally to the product of the synaptic coefficient $P_{rel}$ and the weight of said first excitatory detection synapse.

9. The method according to claim 1, wherein :

each artificial neuron of the intermediate layer is connected to all of the other artificial neurons of the intermediate layer by a plurality of first inhibitory synapses in such a way that a spike emitted by said artificial neuron of the intermediate layer is transmitted to all of the other artificial neurons of the intermediate layer by the plurality of first inhibitory synapses;

each artificial neuron of the output layer is connected to all of the other artificial neurons of the output layer by a plurality of second inhibitory synapses in such a way that a spike emitted by said artificial neuron of the output layer is transmitted to all of the other artificial neurons of the output layer by the plurality of second inhibitory synapses;

when an inhibitory synapse transmits a spike to an artificial neuron of the intermediate layer or of the output layer, said artificial neuron is prevented from emitting a spike for a predefined duration corresponding to an inhibition period and/or the potential of said artificial neuron is decreased proportionally to the weight of said inhibitory synapse.

10. The method according to claim 9, wherein a plurality of second excitatory synapses connects each artificial neuron of the intermediate layer to a plurality of artificial neurons of the output layer, each second excitatory synapse having a weight, wherein:

for each second excitatory synapse, when an artificial neuron of the output layer receives, in a predefined time window, a spike transmitted by said second excitatory synapse and a spike transmitted by a second inhibitory synapse, then the weight of said second excitatory synapse is decreased;

for each second excitatory synapse, when an artificial neuron of the output layer receives, in the predefined time window, a spike transmitted by said second excitatory synapse and no spike transmitted by a second inhibitory synapse, then the weight of said second excitatory synapse is increased.

11. The method according to claim 1, wherein:
each artificial neuron of the output layer has a potential;
each artificial neuron of the output layer emits a spike when its potential exceeds a threshold value;
wherein:
the threshold value of each artificial neuron of the output layer emitting a spike at an instant t is increased proportionally to the number of spikes received by said artificial neuron in a time window around the instant t;
the threshold value Th of each artificial neuron of the output layer emitting a spike at an instant t1 is decreased in such a way that:

$$Th(t2)=\alpha*Th(t1)$$

with Th(t1) the threshold value at the instant t1, Th(t2) the threshold value at an instant t2 later than t1 and $\alpha$ a real number such that $0<\alpha<1$.

12. The method according to claim 1, wherein the network of artificial neurons comprises the input layer, the intermediate layer, a second intermediate layer and the output layer, and according to which:

the input layer transmits the train of first spikes to the intermediate layer and to the second intermediate layer;
the second intermediate layer converts the train of first spikes into a second train of second spikes;
the second intermediate layer transmits the second train of second spikes to the output layer;
as a function of the train of second spikes and the second train of second spikes, the output layer sorts each occurrence of each type of action potential present in the electrical signal.

13. The method according claim 1, wherein the network of artificial neurons comprises the input layer, a second input layer, the intermediate layer and the output layer, and according to which:

the second input layer receives a second electrical signal measuring an electrical activity of a second plurality of biological neurons, the second electrical signal having a variable amplitude as a function of action potentials emitted by the second plurality of biological neurons over time;
the second input layer converts the amplitude of the second electrical signal into a second train of first spikes;
the second input layer transmits the second train of first spikes to the intermediate layer;
the intermediate layer converts the train of first spikes and the second train of first spikes into a train of second spikes.

14. The method according to claim 1, wherein the network of artificial neurons comprises the input layer, a second input layer, the intermediate layer, a second intermediate layer and the output layer, and according to which:

the second input layer receives a second electrical signal measuring an electrical activity of a second plurality of biological neurons, the second electrical signal having a variable amplitude as a function of action potentials emitted by the second plurality of biological neurons over time;
the second input layer converts the amplitude of the second electrical signal into a second train of first spikes;
the second input layer transmits the second train of first spikes to the second intermediate layer;
the second intermediate layer converts the second train of first spikes into a second train of second spikes;
the second intermediate layer transmits the second train of second spikes to the output layer;
as a function of the train of second spikes and of the second train of second spikes, the output layer sorts each occurrence of each type of action potential present in the electrical signal.

15. A network of artificial neurons for the implementation of a method for unsupervised sorting, in real time, of action potentials of a plurality of biological neurons implemented on a neuromorphic circuit, the network of artificial neurons comprising:

an input layer for the reception of an electrical signal having a variable amplitude as a function of action potentials emitted by the plurality of biological neurons over time, the conversion of the electrical signal into a train of first spikes and the transmission of the train of first spikes to an intermediate layer, the input layer being adapted to directly receive the electrical signal measuring the electrical activity of the plurality of biological neurons such that the electrical signal is received by the input layer without being previously encoded or stored outside of said neuromorphic circuit, or both;
said intermediate layer for the conversion of the train of first spikes into a train of second spikes and the transmission of the train of second spikes to an output layer;
said output layer for the sorting, as a function of the train of second spikes, of each occurrence of each type of action potential present in the electrical signal;
each artificial neuron of the input layer being connected to a plurality of artificial neurons of the intermediate layer by a plurality of first excitatory synapses and each artificial neuron of the intermediate layer being connected to a plurality of artificial neurons of the output layer by a plurality of second excitatory synapses, at least one first or second excitatory synapse connecting a first artificial neuron to a second artificial neuron and having a weight that is modified as a function of the instants at which take place presynaptic spikes emitted by the first artificial neuron and postsynaptic spikes emitted by the second artificial neuron.

* * * * *